US007776917B2

(12) United States Patent
Mickle

(10) Patent No.: US 7,776,917 B2
(45) Date of Patent: Aug. 17, 2010

(54) NON-STANDARD AMINO ACID CONJUGATES OF AMPHETAMINE AND PROCESSES FOR MAKING AND USING THE SAME

(76) Inventor: Travis C. Mickle, 3015 Wind Ridge Dr., Iowa City, IA (US) 52241

(*) Notice: Subject to any disclaimer, the term of this patent is extended or adjusted under 35 U.S.C. 154(b) by 7 days.

(21) Appl. No.: 11/953,668

(22) Filed: Dec. 10, 2007

(65) Prior Publication Data
US 2008/0139653 A1 Jun. 12, 2008

Related U.S. Application Data

(60) Provisional application No. 60/869,375, filed on Dec. 11, 2006.

(51) Int. Cl.
*A61K 31/195* (2006.01)
*A61K 31/16* (2006.01)
*A61P 25/00* (2006.01)
(52) U.S. Cl. ...................... 514/561; 514/613
(58) Field of Classification Search ............... 514/625, 514/613
See application file for complete search history.

(56) References Cited

U.S. PATENT DOCUMENTS

| | | | |
|---|---|---|---|
| 2,881,113 A | 4/1959 | Millman | |
| 2,892,753 A * | 6/1959 | Schmidt et al. | 424/48 |
| 6,417,184 B1 | 7/2002 | Ockert | |
| 6,475,494 B2 | 11/2002 | Kaiko et al. | |
| 6,503,950 B1 | 1/2003 | Ockert | |
| 6,525,062 B2 | 2/2003 | Levine | |
| 6,696,066 B2 | 2/2003 | Kaiko et al. | |
| 7,105,486 B2 | 9/2006 | Mickle et al. | |
| 7,223,735 B2 | 5/2007 | Mickle et al. | |
| 2005/0038121 A1* | 2/2005 | Mickle et al. | 514/563 |
| 2005/0054561 A1 | 3/2005 | Mickle et al. | |
| 2006/0177892 A1 | 8/2006 | De Frees | |

FOREIGN PATENT DOCUMENTS

| | | |
|---|---|---|
| FR | 1421130 | 4/1966 |
| WO | 03/072046 | 9/2003 |
| WO | 2007/033099 | 3/2007 |
| WO | 2008/073918 | 6/2008 |
| WO | 2008/098151 | 8/2008 |

OTHER PUBLICATIONS

Amy Sorter, Understanding ADHD Stimulant Abuse, Publication, Vitality Drug Free Work, 2002. (http://12.42.224.168/HealthyLiving/familyhome/jan04familyhomestimulantabuse.htm).
The Drug Enforcement Administration Office of Diversion Control and Office of Congressional and Public Affairs Demand Reduction Section, Stimulant Abuse By School Age Children: A Guide For School Officials; Publication, Developed and Published by The Drug Enforcement Administration Office of Diversion Control and Office of Congressional and Public Affairs Demand Reduction Section; Jun. 2001. (http://www.deadiversion.usdoj.gov/pubs/brochures/stimulant/stimulant_abuse.htm).
G.C. Barrett, D.T. Elmore; Methods for Peptide Bonds Amino Acids and Peptides; 1$^{st}$ Edition, Cambridge University Press, UK, 1998, pp. 151-156.
J. Jones; Amino Acid and Peptide Synthesis; 2$^{nd}$ Edition, Oxford University Press, UK, 2002, pp. 25-41.
European Search Report for European Patent Application No. 07869098.9-2112, dated Dec. 10, 2009.
International Preliminary Report on Patentability for PCT International Application No. PCT/US08/53363, dated Nov. 6, 2008.
Davankova et al., "Synthesis and Pharmacological Properties of N Aminoacyl Derivatives of Beta Phenyl ISO Propylamine." Pharmaceutical Chemistry Journal, vol. 9, No. 3, 1975.
International Search Report and Written Opinion corresponding to International Application Serial No. PCT/US08/53363, mailed Nov. 6, 2008, 19 pages.
Musshoff, "Illegal or legitimate use? Precursor compounds to amphetamine and methamphetamine." Drug Metabolism Reviews 2000 US, vol. 32, No. 1, pp. 15-44.
Office Action in U.S. Appl. No. 12/028,152, dated Feb. 16, 2010.
Office Action in U.S. Appl. No. 12/028,152, dated Feb. 23, 2010.
Office Action in U.S. Appl. No. 12/028,152, dated Mar. 20, 2009.
Office Action in U.S. Appl. No. 12/028,152, dated Nov. 12, 2008.
Office Action in U.S. Appl. No. 12/028,152, dated Nov. 13, 2009.

* cited by examiner

*Primary Examiner*—Sreeni Padmanabhan
*Assistant Examiner*—Sahar Javanmard
(74) *Attorney, Agent, or Firm*—McAndrews, Held & Malloy, Ltd.

(57) ABSTRACT

Disclosed are amphetamine prodrug compositions comprising at least one non-standard amino acid conjugate of amphetamine, a salt thereof, a derivative thereof, or a combination thereof. Methods of making and using the same are also disclosed.

10 Claims, 5 Drawing Sheets

NON-STANDARD AMINO ACID CONJUGATES OF AMPHETAMINE AND PROCESSES FOR MAKING AND USING THE SAME

RELATED APPLICATIONS

This application claims priority to and benefit from U.S. provisional patent application No. 60/869,375, filed on Dec. 11, 2006, which is incorporated hereby in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present technology describes, in general, novel prodrugs/compositions of the stimulant amphetamine (i.e., 1-phenylpropan-2-amine) as well as non-standard amino acid conjugates of amphetamine, salts thereof, other derivatives thereof, and combinations thereof. Additionally, the presently described technology also relates generally to the methods of making and using these new prodrugs/compositions.

The presently described technology in at least one aspect is focused on a slow/sustained controlled release composition of amphetamine, in prodrug form, that allows slow/sustained/controlled delivery of the stimulant into the blood system of a human or animal within a safe therapeutic window upon oral administration. At least some compositions/formulation of the current technology can lessen the rebound effect, cardiovascular stress, addiction/abuse potential and/or other common stimulant side effects associated with amphetamine and similar compounds. Such compositions may also increase the duration of therapeutic efficacy, ease of application, patient compliance and/or any combination of these characteristics when administered, in particular, orally.

Stimulants, including amphetamine and its derivatives, enhance the activity of the sympathetic nervous system and/or central nervous system (CNS) and are prescribed for the treatment of a range of conditions and disorders predominantly encompassing, for example, attention deficit hyperactivity disorder (ADHD), attention deficit disorder (ADD), obesity, narcolepsy, appetite suppression, depression, anxiety and wakefulness.

Attention deficit hyperactivity disorder (ADHD) in children has been treated with stimulants for many years. However, more recently, the increase in number of prescriptions for ADHD therapy in adult population has, at times, outperformed the growth of the pediatric market. Although there are various drugs currently in use for the treatment of ADHD, such as methylphenidate (commercially available from, for example, Novartis International AG (located in Basel, Switzerland) under the trademark Ritalin®) and non-stimulant atomoxetine (commercially from Eli Lilly and Company (located in Indianapolis, Ind.) as Strattera®), amphetamine has been the forerunner in ADHD therapy. Moreover, during classroom trials non-stimulants have shown to be less effective in improving behavior and attention of ADHD afflicted children than amphetamine derivatives.

Initial drug therapy for ADHD was limited to fast acting immediate release formulations of stimulants (e.g., Dexedrine®, pure dextroamphetamine sulfate, commercially available from Smith Kline and French located in the United Kingdom) which triggered an array of potentially undesirable side effects including, for example, fast wear-off of the therapeutic effect of the stimulant active ingredient causing rebound symptoms, cardiovascular stress/disorders (e.g., increased heart rate, hypertension, cardiomyopathy), other side effects (e.g., insomnia, euphoria, psychotic episodes), addiction and abuse.

Behavioral deterioration (rebound/"crashing") is observed in a significant portion of children with ADHD as the medication wears off, typically in the afternoon or early evening. Rebound symptoms include, for example, irritability, crankiness, hyperactivity worse than in the unmedicated state, sadness, crying and in rare cases psychotic episodes. The symptoms may subside quickly or last several hours. Some patients may experience rebound/crashing so severe that treatment must be discontinued. Rebound/crashing effects can also give rise to addictive behavior by enticing patients to administer additional doses of stimulant with the intent to prevent anticipated rebound/crashing negative outcomes and side effects.

Stimulants, such as methylphenidate and amphetamine, have shown to exhibit noradrenergic and dopaminergic effects that can lead to cardiovascular events comprising, for example, increased heart rate, hypertension, palpitations, tachycardia and in isolated cases cardiomyopathy, stroke, myocardial infarction and sudden death. Consequently, currently available stimulants expose patients with pre-existing structural cardiac abnormalities or other severe cardiac indications to even greater health risks and are frequently not used or used with caution in this population. It is notable, however, that the cardiovascular effects of stimulants, for example on heart rate and blood pressure, is dependent on the administered dose. As a result, a treatment which maintains the lowest effective stimulant blood concentrations for a therapeutically beneficial duration is believed to demonstrate fewer cardiovascular risks.

Amphetamine and many of its derivatives (e.g., methamphetamine, 3,4-methylenedioxy-methamphetamine/"Ecstacy") are widely abused for various purposes such as euphoria, extended periods of alertness/wakefulness, or rapid weight loss or by actual ADHD patients who developed excessive self-dosing habits to prevent rebound symptoms from manifesting, for example, in anxiety or depression. The effects desired by potential abusers originated from the stimulation of the central nervous system and prompted a Schedule II or even Schedule I classification for amphetamine (d- and l-amphetamine individually and any combination of both are Schedule II) and certain derivatives thereof after passage of the Controlled Substance Act (CSA) in 1970. Both classifications are defined by the high propensity for abuse. Schedule II drugs have an accepted medical use while Schedule I substances do not pursuant to the CSA. So far, all amphetamine products, including compositions with sustained release formulations and prodrugs thereof, are obligated to include a black box warning on the drug label to inform patients about the potential for amphetamine abuse and dependence.

It has been shown in the conventional art that most side effects of amphetamines are caused by a large initial spike in blood concentration of the stimulant which quickly erodes to levels below therapeutic effectiveness (typically within 4-6 hours). As a consequence, the high potency of dextroamphetamine (d-amphetamine) was subsequently modulated by a series of new drugs with increasingly sustained release profiles achieved by delivering amphetamine more slowly into the blood stream with the goal to create safer and less abusable treatment outcomes and regimens. The methods and technologies for generating smaller spikes in drug blood concentrations include, for example, use of mixed salts and isomer compositions (i.e., different salts of d- and less potent l-amphetamine), extended/controlled/sustained release formulations (e.g., Adderall X® commercially available from Shire U.S., Inc. located in Wayne, Pa.) and, most recently, prodrugs of amphetamine (Vyvanse™ also commercially available from Shire). The ideal drug treatment option should produce stimulant blood concentrations within a narrow therapeutic window for an extended time duration followed by a prolonged fade-out period in order to minimize cardiovascular stress and behavioral deterioration, and would also exhibit anti-abuse properties.

Besides immediate release formulations, newer sustained release formulations have been developed with the objective to provide a therapeutic treatment option that offers the convenience of a single daily dosing regimen versus multiple quotidian administrations. Such formulations also have the objective of imparting or rendering a euphoric response. Sustained release formulations commonly consist of drug particles coated with a polymer or polymer blend that delays and extends the absorption of the active drug substance by the gastrointestinal tract for a relatively defined period of time. Such formulations frequently embed the therapeutic agent/active ingredient/drug within a hydrophilic hydrocolloid gelling polymer matrix (e.g., hydroxypropyl methylcellulose, hydroxypropyl cellulose or pullulan). This dosage formulation in turn becomes a gel upon entering an acidic medium, as found in the stomach of humans and animals, thereupon slowly effusing the therapeutic agent/active ingredient/drug. However, the dosage formulation dissolves in an alkaline medium, as found in the intestines of humans and animals, concurrently liberating the drug more quickly in an uncontrolled manner. Some formulations, such as acrylic resins, acrylic latex dispersions, cellulose acetate phthalate, and hydroxypropyl methylcellulose phthalate, offer improved sustained release in the intestines by being resistant to acidic environments and dispensing the active ingredient only at elevated pH via a diffusion-erosion mechanism, either by themselves or mixed with hydrophilic polymers.

Sustained release formulations have been moderately effective in providing an improved and extended dosage form over immediate release tablets. Nonetheless, such formulations are potentially subject to inconsistent, erratic or premature release of the therapeutic agent due to failure of the polymer material and they also usually allow easy extraction of the active ingredient utilizing a simple physical procedure. Since single daily dose formulations contain a greater amount of amphetamine than immediate release formulations, they are more attractive to potential abusers, consequently making the extractability of drug substance an additional undesirable property. It is also, at least in part, a reason for increased drug diversion, especially evident by selling or trading of medication by school children who are ADHD patients and in possession of sustained release amphetamine capsules. The obtained stimulants are then abused by classmates without the disorder by either ingesting high doses or snorting the drug material after crushing it.

U.S. Pat. No. 7,105,486 (to assignee New River Pharmaceuticals, hereinafter the "'486 patent") appears to describe compounds comprising a chemical moiety (namely L-lysine) covalently attached to amphetamine, compositions thereof, and methods of using the same. Allegedly, these compounds and their compositions are useful for reducing or preventing abuse and overdose of amphetamine. The '486 patent also describes that using any amino acid other than l-lysine (Table 46) will not give rise to the same in vivo properties demonstrated by l-lysine-d-amphetamine (Lys-Amp, Vyvanse™). Additionally, since lysine is a natural and standard amino acid, the breakdown of the new prodrug occurs faster than desired to reduce the side effect profile. Thus, quick release of amphetamine from such standard amino acid conjugate compositions may cause an increase in blood pressure and heart rate found in other conventional stimulant treatments. As a result, there still exists a need within the art for a safer dosage form of amphetamine, and treatment regimen that is therapeutically effective and can provide sustained release and sustained therapeutic effect

BRIEF SUMMARY OF THE INVENTION

The presently described technology provides, in part, compositions comprising at least one amphetamine conjugated with a non-standard amino acid, or a salt thereof, which can diminish or eliminate pharmacological activity of the amphetamine until released in vivo. The non-standard amino acid conjugate(s) of the present technology is amphetamine in a prodrug form, and can be converted into its active form in the body by normal metabolic processes. Although not wanting to be bound by any particular theory, one or more non-standard amino acid conjugates of the present technology are believed to be safer than other sustained release forms of amphetamine by providing controlled blood levels for a prolonged period of time, thus preventing the rebound effect, cardiovascular stress and euphoria associated with conventional stimulant treatment options.

The presently described technology further provides methods of controlled therapeutic delivery of amphetamine compositions by oral administration. Release of amphetamine following oral administration of the non-standard amino acid conjugates of the present technology can occur gradually over an extended period of time thereby eliminating unintended elevations (e.g., blood level concentration spikes) of drug levels in the bloodstream of a human or animal patient. Again not wanting to be bound by any particular theory, it is also believed that such spikes in blood levels can lead to a euphoric drug "high" and cardiovascular effects like increased blood pressure and heart rate. Additionally, sustained blood levels are achieved within an effective therapeutic range for a longer duration than other conventional therapies, thereby preventing a rebound effect.

At least some compositions comprising the amphetamine prodrugs of the present technology are resistant to abuse by parenteral routes of administration, such as intravenous "shooting," intranasal "snorting," or inhalation "smoking," that are often employed during illicit use. The present technology thus provides a stimulant based treatment modality and dosage form for certain disorders requiring the stimulation of the CNS such as ADHD, ADD, obesity, narcolepsy, appetite suppressant, depression, anxiety, and wakefulness with reduced or prevented abuse potential. Although not wanting to be bound by any particular theory, it is believed that the treatment of such CNS conditions as noted above with compositions of the present technology results in substantially decreased abuse liability as compared to existing stimulant treatment modalities and dosage forms.

At least some compositions comprising the amphetamine prodrugs of the present technology can also be used for treating stimulant (cocaine, methamphetamine) abuse and addiction, for improving battle field alertness, and/or for combating fatigue.

In a first aspect, the presently described technology provides a composition comprising at least one non-standard amino acid conjugate of amphetamine, a salt thereof, a derivative thereof, or a combination thereof. Preferably, the non-standard amino acid is covalently attached to amphetamine through the C-terminus of the non-standard amino acid. The N-terminus or the side chain amino group of the non-standard amino acid may be in a free and unprotected state, or in the form of a salt thereof. The non-standard amino acid moiety can be derived from a non-standard amino acid that is either a dextro- (d-) or levo- (l-) form amino acid, racemic amino acid, or a mixture thereof.

In accordance with some embodiments, non-standard amino acids are used. Examples of preferred non-standard amino acids to be conjugated with the amphetamine include, but are not limited to, ornithine, homoarginine, selenomethionine, citrulline, sarcosine, homoserine, and homocitrulline. More preferred non-standard amino acids for at least some embodiments of the present technology are homoarginine and ornithine. Homoarginine is most preferred for at least some embodiments of the present technology.

The compositions of the present technology preferably have no or a substantially decreased pharmacological activity when administered through injection or intranasal routes of administration. However, they remain orally bioavailable. The bioavailability can be a result of the hydrolysis of the covalent linkage following oral administration. Hydrolysis is time-dependent, thereby allowing amphetamine and other metabolites such asp-hydroxyamphetamine and p-hydroxyephedrine to become available in its active form over an extended period of time. In at least one further embodiment, release of amphetamine is diminished or eliminated when the composition of the present technology is delivered by parenteral routes.

For example, in one embodiment, the composition of the present technology maintains its effectiveness and abuse resistance following the crushing of the tablet, capsule or other oral dosage form utilized to deliver the therapeutic component (i.e., active ingredient/drug) due to the inherent controlled release components being a property of the composition not formulation. In contrast, conventional extended release formulations used to control the release of amphetamine are subject to release of up to the entire amphetamine content immediately following crushing. When the content of the crushed tablet is injected or snorted, the large dose of amphetamine produces the "rush" effect sought by addicts.

In another aspect, the presently described technology provides a method for treating a human or animal patient with a disorder or condition requiring the stimulation of the patient's CNS (Central Nervous System), comprising the step of orally administering to the patient in need a composition formulated for oral dosage comprising at least one non-standard amino acid conjugate of amphetamine of the present technology, wherein the blood levels of amphetamine in the patient's body can maintain a therapeutically effect level throughout a given day, and do not lead to behavioral deterioration or the rebound effect.

In another aspect, the presently described technology provides a method for treating a human or animal patient with a disorder or condition requiring the stimulation of the patient's CNS (Central Nervous System), comprising the step of orally administering to the patient in need a composition formulated for oral dosage comprising at least one non-standard amino acid conjugate of amphetamine of the present technology, wherein the blood levels of amphetamine in the patient's body are not unnecessarily elevated (i.e., blood level spikes) thus preventing additional cardiovascular stress through, for example, increased blood pressure and/or heart rate.

In another aspect, the presently described technology provides a method for treating a human or animal patient with a disorder or condition requiring the stimulation of the patient's CNS, comprising orally administering to the patient in need a composition formulated for oral dosage comprising at least one non-standard amino acid conjugate of amphetamine, wherein the blood levels of amphetamine in the patient's body can maintain a therapeutically effect level, but do not result in an euphoric effect (such as that observed with abuse of amphetamines).

In a further aspect, the presently described technology provides a method for delivering amphetamine, comprising providing a human or animal patient with a therapeutically effective amount of at least one non-standard amino acid conjugate of amphetamine, which can provide a therapeutically bioequivalent area under the curve (AUC) when compared to free amphetamine, but does not provide a concentration max ($C_{max}$) which results in an increased heart rate, increased blood pressure or drug related euphoria when taken orally.

Other objects, advantages and embodiments of the invention are described below and will be obvious from this description and practice of the invention.

DETAILED DESCRIPTION OF THE INVENTION

Figure 1:
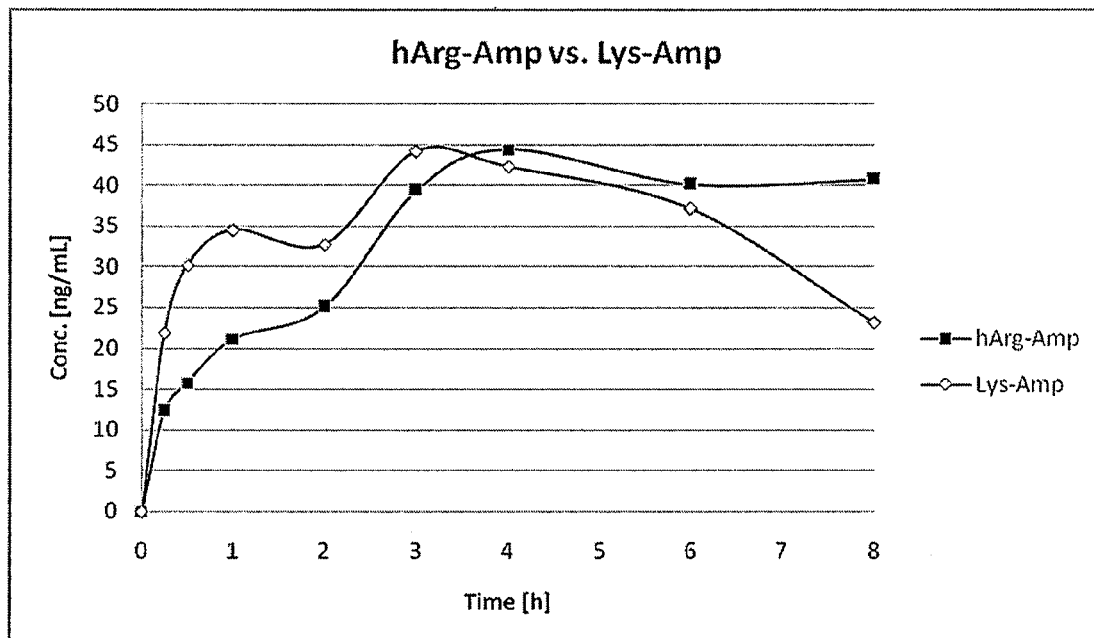
FIG. 1 shows the mean plasma concentration curves (n=5) of d-amphetamine released by l-homoarginine-d-amphetamine or l-lysine-d-amphetamine in the biological oral study of Example 7.

The presently described technology relates to novel prodrugs/compositions of amphetamine, more specifically to non-standard amino acid conjugates of amphetamine, salts thereof, derivatives thereof, or combinations thereof. Methods of making and using the prodrugs/compositions of the present technology are also disclosed.

As used herein, a "non-standard" amino acid refers to an amino acid that is not one of the "standard" 20 amino acids and they may be derived from either natural or synthetic sources. "Non-standard" amino acids are non-essential, and are not readily incorporated into proteins of natural origin. They are either metabolites or precursors in various metabolic pathways. With the exception of selenocysteine, there is no human genetic codon for the formation of non-standard amino acids. For example, the diamino acid lysine is a standard, essential amino acid, and is therefore excluded from the scope of the presently described technology.

As used herein, "amphetamine" shall mean any of the sympathomimetic phenethylamine derivatives which have central nervous system stimulant activity, including, but not limited to, amphetamine (alpha-methyl-phenethylamine), methamphetamine, p-methoxyamphetamine, methylenedioxyamphetamine, 2,5-dimethoxy-4-methylamphetamine, 2,4,5-trimethoxyamphetamine, 3,4-methylenedioxy-methamphetamine, and methylphenidate.

As used herein, "in a manner inconsistent with the manufacturer's instructions" or similar expression is meant to include, but is not limited to, consuming amounts greater than amounts described on the label or ordered by a licensed physician, and/or altering by any means (e.g., crushing, breaking, melting, separating, etc.) the dosage formulation such that the composition may be injected, inhaled or smoked.

As used herein, the phrases such as "decreased," "reduced," "diminished" or "lowered" is meant to include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or increments therein.

In accordance with some embodiments, the present technology provides amphetamine in a prodrug form. More specifically, the amphetamine prodrug comprises at least one non-standard amino acid covalently bonded or attached to amphetamine, which includes different forms or modified forms of sympathomimetic phenethylamine derivatives. According to the presently described technology, any non-standard amino acid can be used to produce the amino acid conjugate of amphetamine. The amino acid can be either the dextro- (d-) or levo- (l-) form of the amino acid, a racemic mixture of the amino acid, or a mixture thereof.

In some embodiments, non-standard amino acids are used to produce the amino acid conjugates of amphetamine. One group of preferred non-standard amino acids suitable for the presently described technology can be represented by the following general formula:

NH$_2$—CH(R)—COOH wherein R is a side chain of one of the non-standard amino acids. In some preferred embodiments, R comprises the side chain of ornithine (—CH$_2$CH$_2$CH$_2$NH$_2$) or homoarginine (—CH$_2$CH$_2$CH$_2$CH$_2$NH—(C=NH)—NH$_2$). In some alternative embodiments, R can comprise the side chain of any other non-standard amino acid.

In accordance with the presently described technology, the non-standard amino acid is attached to amphetamine to make the non-standard amino acid conjugate of amphetamine or salts thereof. Preferably, the non-standard amino acid is covalently attached to amphetamine through the C-terminus of the amino acid. The N-terminus or, when it is present, the side chain amino group of the amino acid may be in a free and unprotected state, or in the form of a salt thereof. Alternatively, in some embodiments, the non-standard amino acid can be attached to amphetamine through the N-terminus. Examples of salts of non-standard amino acid conjugates of amphetamine that can be formed and administered to patients in accordance with the presently described technology include, but are not limited to, mesylate, hydrochloride, sulfate, oxalate, triflate, citrate, malate, tartrate, phosphate, nitrate, and benzoate salts, and mixtures thereof.

Some of the preferred non-standard amino acid conjugates of amphetamine of the present technology can be represented by the following general formula,

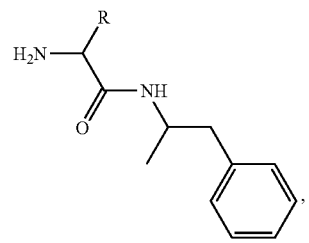

wherein R=the side chain of any non-standard amino acid. More preferably, R is homoarginine or ornithine due to their low toxicity profile in humans and animals.

Examples of non-standard amino acids that are contemplated for the presently described technology include, but are not limited to: ornithine, homoarginine, pyrrolysine, lanthionine, 2-aminoisobutyric acid, dehydroalanine, B-alanine, homocysteine, homoserine, 2-oxoarginine, gamma-aminobutyric acid (GABA), 4-amino butanoic acid, all phosphorylated standard amino acids, all hydroxylated standard amino acids, all acetylated standard amino acids, all succinated standard amino acids, all methylated standard amino acids, LL-2,6-diaminopimelic acid, 6-aminohexanoic acid, L-2-aminoadipate 6-semialdehyde, pipecolic acid, D-threo-2,4-diaminopentanoate, 2-amino-4-oxopentanoic acid, L-erythro-3,5-diaminohexanoic acid, (S)-5-amino-3-oxo-hexanoic acid, N6-hydroxy-L-lysine, N6-acyl-L-lysine, L-saccharopine, 5-aminovaleric acid, N6-methyl-L-lysine, N6,N6-dimethyl-L-lysine, N6,N6,N6-trimethyl-L-lysine, 3-hydroxy-N6,N6,N6-trimethyl-L-lysine, 4-trimethylammoniobutanoic acid, 5-hydroxy-L-lysine, L-citrulline, 2-oxo-4-hydroxy-5-aminovalerate, pyrrole-2-carboxylate, L-erythro-4-hydroxyglutamic acid, trans-4-hydroxy-L-proline, 4-oxoproline, N-methylglycine (sarcosine), 3-sulfino-L-alanine, O3-acetyl-L-serine, selenomethionine, selenocysteine, Se-methylselenomethionine, Se-methylselenocysteine, selenocystathionine, selenocysteine selenate, and cystathione.

Some structural examples of non-standard amino acids are shown below:

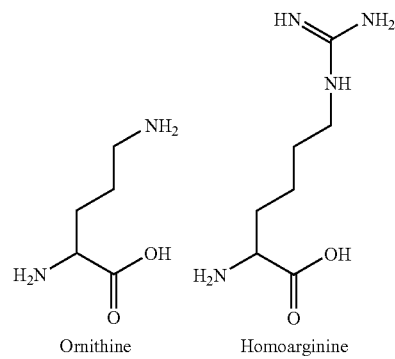

Ornithine          Homoarginine

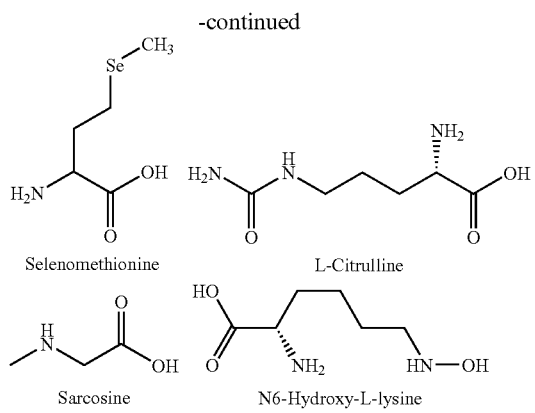

Preferred non-standard amino acids for the present technology include, but are not limited to, ornithine, homoarginine, selenomethionine, citrulline, sarcosine, homoserine, and homocitrulline. For at least some embodiments, homoarginine and ornithine are more preferred. Homoarginine is most preferred for at least some embodiments of the present technology.

The amphetamine can be in d-form, l-form, or racemic form, or can be a mixture thereof. For example, when l-ornithine (l-2,5-diaminopentanoic acid) is used, it can be chemically conjugated to a d- or l-amphetamine to produce a novel prodrug of amphetamine (e.g., 2,5-diamino-N(1-phenylpropan-2-yl)pentanamide).

To conjugate a non-standard amino acid with amphetamine, the one or more amino groups are preferably protected before the amino acid is reacted with amphetamine. The non-standard amino acid whose amino group(s) are protected can be referred to as an N-protected amino acid. Agents and methods for protecting amino groups in a reactant are known in the art. One can either protect the amino groups prior to reaction, or use commercially available N-protected amino acids directly. Preferably, the carboxylic acid group in the N-protected amino acid is activated by an acid activating agent to help the reaction of the N-protected amino acid with amphetamine. General information about the reaction of amino acids to form peptide bonds can be found in, for example, G. C. Barett, D. T. Elmare, Amino Acids and Peptides, page 151-156, Cambridge University Press, UK (1st edition, 1998); Jones, J., Amino Acid and Peptide Synthesis, pages 25-41, Oxford University Press, UK (2nd edition, 2002), which are incorporated herein by reference in their entirety.

One category of acid activating agent well known in the art is carbodiimides. Examples of carbodiimide acid activating agents include, but are not limited to, dicyclohexylcarbodiimide (DCC), 1-ethyl-3-(3'-dimethylaminopropyl)-carbodiimide (EDCI), and diisopropylcarbodiimide (DIPCDI). The N-protected amino acid conjugate of amphetamine resulting from the reaction of the N-protected amino acid and amphetamine can then be de- or un-protected with a strong acid to produce the corresponding final salt form of the non-standard amino acid conjugate of amphetamine. Scheme 1 below shows a general synthetic scheme when ornithine is used as the non-standard amino acid.

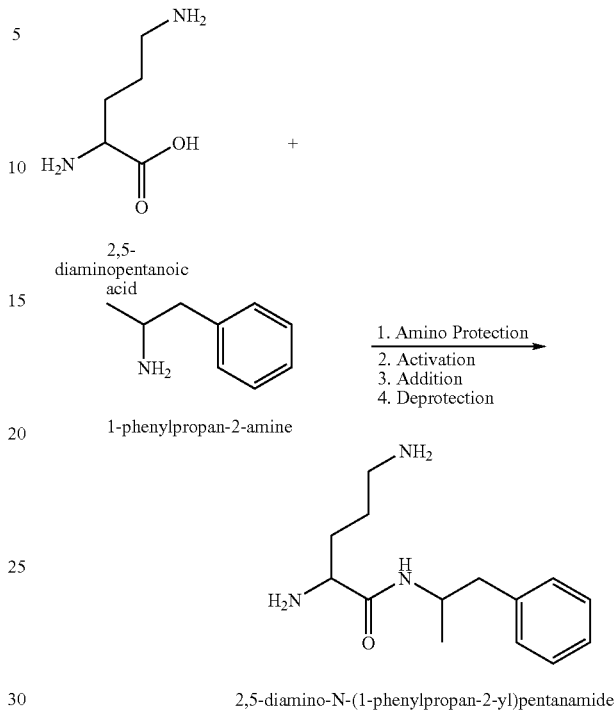

In accordance with some embodiments of the presently described technology, d-amphetamine (dextroamphetamine) is preferably used and l-ornithine is a preferred non-standard amino acid. In accordance with some other embodiments, the prodrug of d-amphetamine can be used in combination with a prodrug of l-amphetamine or l-amphetamine itself.

In accordance with some other preferred embodiments, synthesis of Orn-Amp (l-ornithine-d-amphetamine) can be accomplished in two steps as shown in reaction Scheme 2 below. The first step is the coupling of Boc-Orn(Boc)-OH with d-amphetamine using EDCI. N-hydroxysuccinimide (NHS) can be added to form an in-situ activated ester with diisopropylethylamine (DIPEA) used as a co-base. The product can then be subjected to deprotection with methanesulfonic acid which also forms the corresponding dimesylate salt.

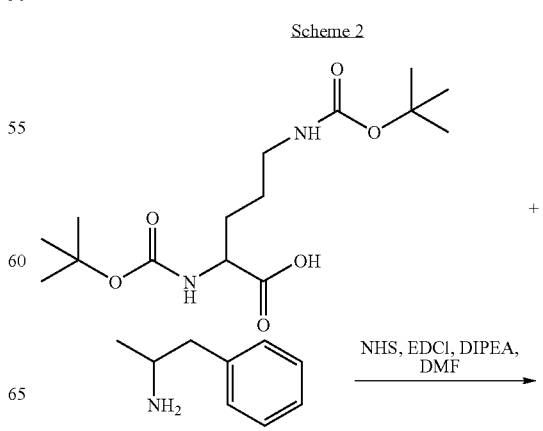

-continued

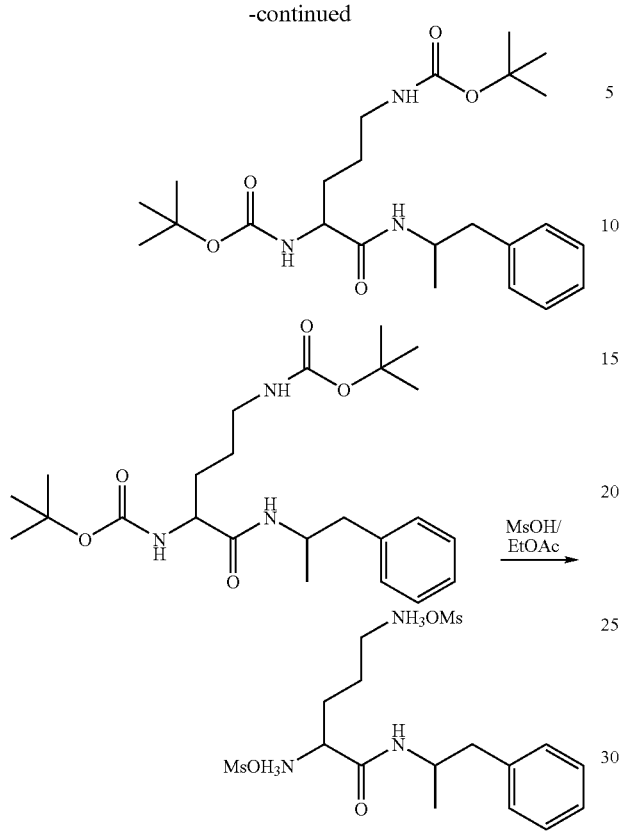

Besides ethyl acetate, examples of other solvents that can be used in the presently described technology include, but are not limited to, isopropyl acetate (IPAC), acetone, and dichloromethane (DCM). A mixture of different solvents can also be used. When a polar solvent is required, water, dimethylformamide (DMF), 1,4-dioxane or dimethylsulfoxide (DMSO) can be used. Co-bases such as tertiary amines may or may not be added in the coupling reaction. Examples of suitable co-bases include 1-methylmorpholine (NMM), triethylamine (TEA), etc.

It is important to note that preparation of Orn-Amp requires additional experimentation compared to the prior art. It has been surprisingly found that significant changes of the solubility in starting material of Boc-Orn(Boc)-OH required the use of DMF instead of less polar solvents stated previously. In addition, due to the unique solubility differences of Orn-Amp 2MsOH as compared to either Lys-Amp 2HCl or Lys-Amp 2MsOH, the procedures of the conventional art would not give rise to Orn-Amp 2MsOH without significant experimentation. Also, formation of the free base of amphetamine was performed in situ and was not isolated. The formation of the activated ester was performed in situ with the addition reaction following in the same reaction vessel. Quite surprisingly, these changes to solubility and reaction conditions are not readily apparent from previously published procedures or from the overall structures themselves and were unpredictable and unexpected which lead to the discovery of the presently described technology.

In accordance with some other preferred embodiments, synthesis of l-homoarginine-d-amphetamine dihydrochloride (hArg-Amp) can be accomplished in three steps as shown in Scheme 3 below. In the first step, an N-protected hArg (e.g., Boc-hArg(NO₂)) is coupled with d-amphetamine using EDCI. NHS is added to form an in-situ activated ester with DIPEA used as a co-base. The product is then subjected to hydrogenation under acidic conditions followed by deprotection with hydrochloric acid which forms the corresponding dihydrochloride salt.

Scheme 3

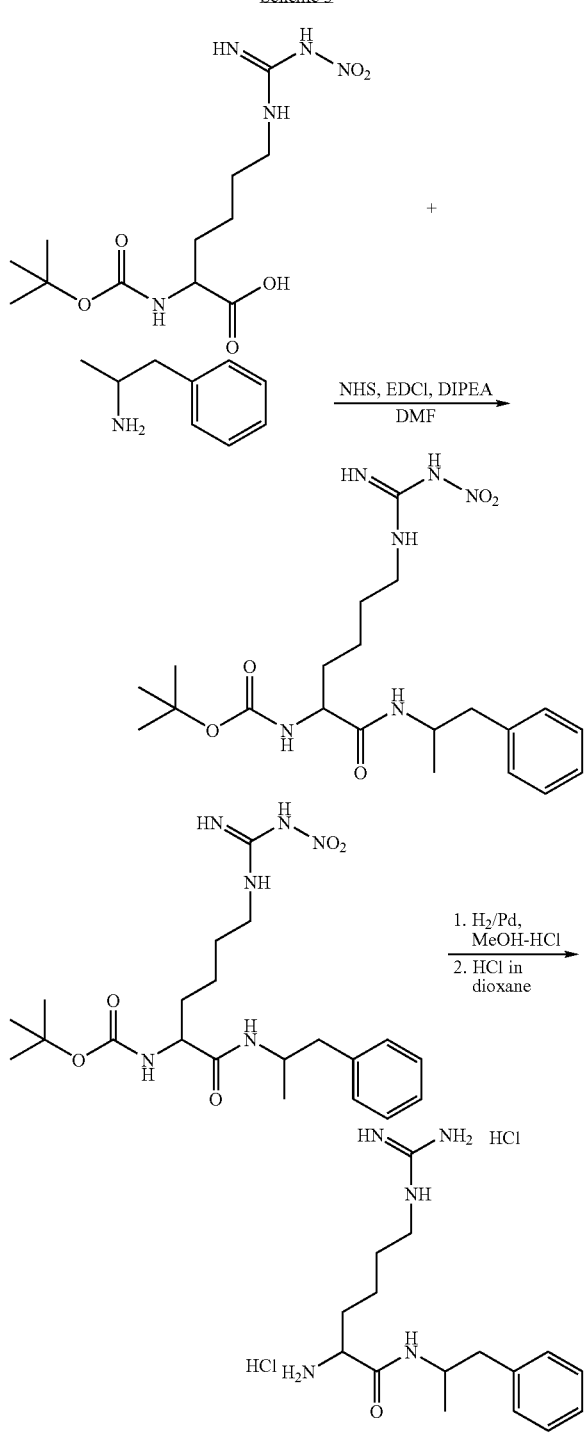

The preparation of hArg-Amp required extensive modifications to previously published methods and syntheses. First, Boc-hArg(NO₂)—OH required use of DMF to solubilize the material prior to reaction. Second, formation of the free base of amphetamine was performed in situ and was not isolated. Also, the formation of the activated ester was performed in situ with the addition reaction following in the same reaction vessel. Homoarginine is different from other standard and non-standard amino acids in that it requires a separate step of deprotection to remove the nitro group from the side chain. Failure to do so correctly can lead to undesirable products that do not perform in vivo with respect to the desired therapeutic outcomes discussed herein.

In some other preferred embodiments of the present technology, l-citrulline-d-amphetamine hydrochloride (Cit-Amp) can be synthesized as shown in reaction Scheme 4 below in three overall steps. The first step involves the activation of Boc-Cit-OH to form an activated ester using DCC and NHS followed by the addition of d-amphetamine to produce the protected Boc-Cit-Amp. Deprotection using 4N HCl in dioxane gives the corresponding hydrochloride salt.

Scheme 4

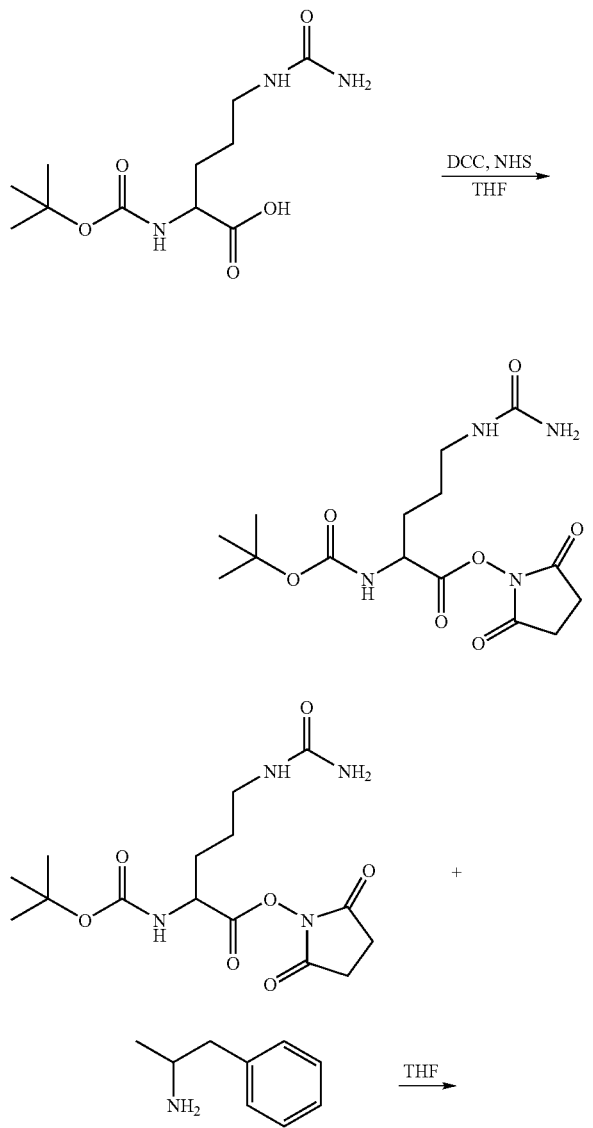

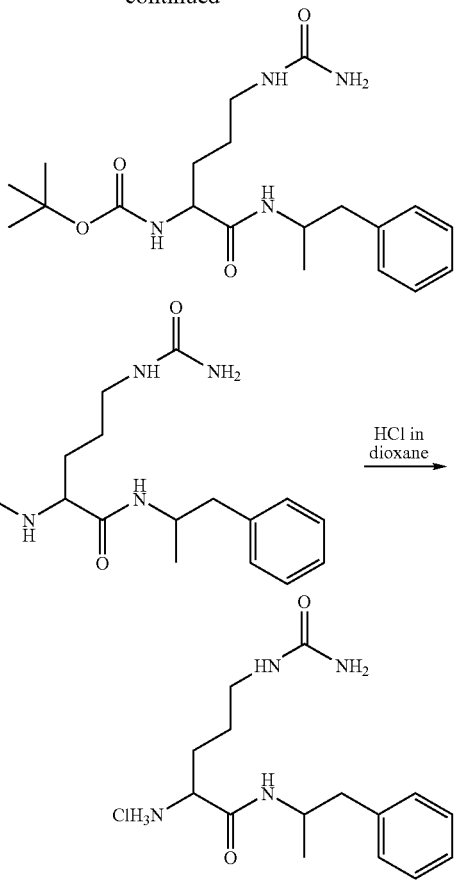

At least some compounds of the present technology have no or a substantially decreased pharmacological activity when delivered through alternative routes of administration like intranasal or intravenous. However, they remain orally bioavailable at a level similar or slightly lower than other controlled release forms. The bioavailability can be a result of the hydrolysis of the covalent linkage following oral administration. Hydrolysis is time-dependent, thereby allowing amphetamine to become available in its active form over an extended period of time in a very controlled fashion. Therefore, the compounds of the present technology can release amphetamine over an extended period and provide a therapeutically bioequivalent area under the curve (AUC) when compared to other controlled release forms of amphetamine (Adderall X® or Vyvanse™), with little or no spike in concentration max ($C_{max}$) or equivalent $C_{max}$. Not wanting to be bound by any particular theory, it is believed that since non-standard amino acids are used to produce the prodrug, the in vivo breakdown of the prodrug by enzymes would occur at a slower rate than, for example, when a standard amino acid is used to conjugate amphetamine. This will allow the prodrug to release amphetamine slowly and, preferably, only under in vivo conditions.

As a person of ordinary skill in the art will understand, drug products are considered pharmaceutical equivalents if they contain the same active ingredient(s), are of the same dosage form, route of administration and are identical in strength or concentration. Pharmaceutically equivalent drug products are formulated to contain the same amount of active ingredient in the same dosage form and to meet the same or compendial or other applicable standards (i.e., strength, quality, purity, and identity), but they may differ in characteristics such as shape, scoring configuration, release mechanisms, packaging, excipients (including colors, flavors, preservatives), expiration time, and, with certain limits, labeling. Drug products are considered to be therapeutic equivalents only if they are pharmaceutical equivalents and if they can be expected to have the same clinical effect and safety profile when administered to patients under the conditions specified in the labeling. The term "bioequivalent," on the other hand, describes pharmaceutical equivalent or pharmaceutical alternative products that display comparable bioavailability when studied under similar experimental conditions.

Standard amino acids such as lysine are not contemplated for the presently described technology, because lysine is an essential part of all dietary requirements, it would be expected that the prodrug conjugated with lysine would be released at a faster rate. By using non-standard amino acids, the release rate of amphetamine will be reduced due to the difference in overall digestion rate of non-standard amino acid conjugates of amphetamine versus standard amino acid conjugates of amphetamine such as lysine-amphetamine conjugate. This reduction in the rate of hydrolysis will decrease the incidence of cardiac side effects including higher blood pressure, rapid heart rate, and/or other subsequent side effects associated with conventional amphetamine treatment.

In accordance with the presently described technology, release of amphetamine after oral administration of the prodrug of the presently described technology would occur under desired physiological conditions. Preferably, other routes of administration (e.g., intranasal or intravenous) do not break the prodrug down to any appreciable extent. Also preferably, external means (chemical, enzymatic or other) will not break the prodrug down to any appreciable extent either. The breakdown ratio of the prodrug that can be achieved through external means is preferably less than about 50%, alternatively less than about 25%, alternatively less than about 20%, alternatively less than about 10%.

The presently described technology utilizes covalent modification of amphetamine by a non-standard amino acid to decrease its potential for causing behavioral deterioration or the rebound effect. It is believed that since the amphetamine is covalently modified to form the non-standard amino acid conjugate of the present technology and releases slowly over the entire length of the day, little or no rebound effect can occur due to the slow continuous release of the active ingredient/drug/therapeutic component.

Compounds, compositions and methods of the presently described technology are also believed to provide reduced potential for rebound, reduced potential for abuse or addiction, and/or improve amphetamine's stimulant related toxicities. By limiting the blood level spike, doses are kept at levels required for a clinically significant effect without the unnecessary levels administered with other therapies. It is widely held that these spikes in blood levels can lead to cardiovascular toxicity in the form of higher blood pressure and rapid heart rate in addition to the euphoria encountered in drug abuse. Also, with a full day therapy, the risk of re-dosing is lowered, thus preventing additional toxicities or drug abuse issues.

The amphetamine prodrugs of the presently described technology could be used for any condition requiring the stimulation of the central nervous system (CNS). These conditions include, for example, attention deficit hyperactivity disorder (ADHD), attention deficit disorder (ADD), obesity, narcolepsy, appetite suppressant, depression, anxiety, and wakefulness. Amphetamine stimulants have also demonstrated usefulness in treating stimulant (e.g., cocaine, methamphetamine) abuse and addiction. Amphetamine stimulants have also been used extensively to improve battle field alertness and to combat fatigue.

Therefore, in accordance with some embodiments, the presently described technology provides amphetamine compositions comprising at least one amphetamine prodrug of the present technology.

One embodiment is a composition that can prevent behavioral deterioration of amphetamine dosing comprising at least one non-standard amino acid conjugate of amphetamine.

Another embodiment is a composition for safely delivering amphetamine, comprising a therapeutically effective amount of at least one non-standard amino acid conjugate of amphetamine wherein the non-standard amino acid moiety can reduce the rate of absorption of the amphetamine as compared to delivering the unconjugated amphetamine or amphetamine conjugated to a standard amino acid.

Another embodiment of the present technology is a composition that can reduce amphetamine toxicity, comprising at least one non-standard amino acid conjugate of amphetamine wherein the non-standard amino acid moiety can release amphetamine over the entire course of a day providing a limited behavioral deterioration effect.

Another embodiment of the present technology is a composition that can reduce amphetamine toxicity, comprising at least one non-standard amino acid conjugate of amphetamine wherein the non-standard amino acid moiety can provide a serum release curve which does not increase above amphetamine's therapeutic level and does not cause blood level spiking.

Another embodiment of the present technology is a composition that can reduce bioavailability of amphetamine or prevent a toxic release profile in a patient, comprising at least one non-standard amino acid conjugate of amphetamine wherein the non-standard amino acid conjugate of amphetamine can maintain a steady-state serum release curve which can provide a therapeutically effective bioavailability but prevent spiking or increased blood serum concentrations compared to unconjugated amphetamine or amphetamine conjugated with a standard amino acid.

Another embodiment of the present technology is a composition comprising at least one non-standard amino acid conjugate of amphetamine that can prevent a $C_{max}$ or equivalent $C_{max}$ spike for amphetamine.

Another embodiment of the present technology is a composition comprising at least one non-standard amino acid conjugate of amphetamine that can prevent a $C_{max}$ or equivalent $C_{max}$ spike for amphetamine when taken by means other than orally while still providing a therapeutically effective bioavailability curve if taken orally.

In one or more embodiments, the non-standard amino acid conjugates of amphetamine of the present technology may further comprise a polymer blend which comprises a hydrophilic polymer and/or a water-insoluble polymer. The polymers may be used according to industry standards to further enhance the sustained release/abuse resistant properties of the amphetamine prodrug of the present technology without reducing the abuse resistance. For instance, a composition might include: about 70% to about 100% amphetamine prodrug of the present technology by weight, from about 0.01% to about 10% of a hydrophilic polymer (e.g. hydroxypropyl methylcellulose), from about 0.01% to about 2.5% of a water-insoluble polymer (e.g. acrylic resin), from about 0.01% to about 1.5% of additives (e.g. magnesium stearate), and from about 0.01% to about 1% colorant by weight.

Hydrophilic polymers suitable for use in the sustained release formulations include one or more natural or partially or totally synthetic hydrophilic gums such as acacia, gum tragacanth, locust bean gum, guar gum, or karaya gum, modified cellulosic substances such as methylcellulose, hydroxymethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art, or a combination of such polymers. These hydrophilic polymers gel and would dissolve slowly in aqueous acidic media thereby allowing the amphetamine conjugate to diffuse from the gel in the stomach. When the gel reaches the intestines it would dissolve in controlled quantities in the higher pH medium to allow further sustained release. Preferred hydrophilic polymers are the hydroxypropyl methylcelluloses such as those manufactured by The Dow Chemical Company and known as Methocel ethers, such as Methocel E1OM.

Other formulations according to one or more embodiments of the present technology may further comprise pharmaceutical additives including, but not limited to, lubricants such as magnesium stearate, calcium stearate, zinc stearate, powdered stearic acid, hydrogenated vegetable oils, talc, polyethylene glycol, and mineral oil; colorants such as Emerald Green Lake, FD&C Red No. 40, FD&C Yellow No. 6, D&C Yellow No. 10, or FD&C Blue No. 1 and other various certified color additives (See 21 CFR, Part 74); binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quaternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. In one preferred embodiment, a sustained release formulation of the present technology further comprises magnesium stearate and Emerald Green Lake.

The amphetamine compositions of the present technology, which comprises at least one amphetamine prodrug of the present technology and can be further formulated with excipients, may be manufactured according to any appropriate method known to those of skill in the art of pharmaceutical manufacture. For instance, the amphetamine prodrug and a hydrophilic polymer may be mixed in a mixer with an aliquot of water to form a wet granulation. The granulation may be dried to obtain hydrophilic polymer encapsulated granules of the amphetamine prodrug. The resulting granulation may be milled, screened, then blended with various pharmaceutical additives such as, water insoluble polymers, and/or additional hydrophilic polymers. The formulation may then be tableted and may further be film coated with a protective coating which rapidly dissolves or disperses in gastric juices.

It should be noted that the above additives are not required for the amphetamine composition of the present technology to have sustained release in vivo properties. The non-standard amino acid conjugates of the present technology are chemically stable to in vitro hydrolysis of the amide linkage to prevent tampering or removing the amphetamine prior to oral ingestion. Also, the controlled release of amphetamine through oral administration of the non-standard amino acid conjugate of the present technology is an inherent property of the molecule, not related to the formulation. Put another way, the amphetamine prodrug of the present technology itself can control the release of amphetamine into the digestive tract over an extended period of time resulting in an improved profile when compared to immediate release combinations and prevention of abuse without the addition of the above additives. Therefore, the prodrug of the present technology can be easily formulated to different dosage forms. In one or more embodiments of the present technology, no further sustained release additives are required to achieve a blunted or reduced pharmacokinetic curve (e.g., reduced euphoric effect) while achieving therapeutically effective amounts of amphetamine release when taken orally.

The compounds and compositions of the presently described technology can be formulated into and administered by a variety of dosage forms through any oral routes of delivery. Once administered, the prodrugs will release amphetamine under digestive conditions. Any biologically-acceptable dosage form known to persons of ordinary skill in the art, and combinations thereof, are contemplated. Examples of preferred dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, oral films (e.g., fast dissolving thin strips), and combinations thereof. Preferred dosage forms include capsule, solution formulation, and fast dissolving oral film.

Formulations of the present technology suitable for oral administration can be presented as discrete units, such as capsules, caplets, tablets, or oral films. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow.

If the capsule form is chosen, for example, excipients used in the capsule formulation could be broken up into four separate groups: bulk agent/binder, disintegrant, lubricant and carrier. A preferred capsule formulation comprises from about 50% to about 90% by weight a bulk agent such as various types of microcrystalline cellulose, from about 1% to about 5% by weight of a disintegrant such as croscarmellose sodium, from about 0.5% to about 2.5% of a lubricant such as magnesium state or other fatty acid salts. The carrier can be either hard gelatin capsules, and preferably use the smaller size ones such as #3 or #4 hard gelatin capsules.

Soft gel or soft gelatin capsules may be prepared, for example, by dispersing the formulation of the present technology in an appropriate vehicle (vegetable oils are commonly used) to form a high viscosity mixture. This mixture can then be encapsulated with a gelatin based film using technology and machinery known to those in the soft gel industry. The industrial units so formed are then dried to constant weight.

Chewable tablets, for example, may be prepared by mixing the formulations of the present technology with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film-coated tablets, for example, may be prepared by coating tablets using techniques such as rotating pan coating methods or air suspension methods to deposit a contiguous film layer on a tablet.

Compressed tablets, for example, may be prepared by mixing the formulation of the present technology with excipients intended to add binding qualities to disintegration qualities. The mixture can be either directly compressed or granulated then compressed using methods and machinery known to those in the industry. The resultant compressed tablet dosage units are then packaged according to market need, i.e., unit dose, rolls, bulk bottles, blister packs, etc.

One preferred formulation of the non-standard amino acids is a fast dissolving oral film or thin strip. Methods and other ingredients needed to make oral films or thin strips are known in the art. Potential film forming agents include pullulan, hydroxypropylmethyl cellulose, hydroxypropyl cellulose, polyvinyl pyrrolidone, polyvinyl alcohol, sodium alginate, polyethylene glycol, xanthan gum, tragacanth gum, guar gum, acacia gum, Arabic gum, polyacrylic acid, amylase, starch, dextrin, pectin, chitin, chitosin, levan, elsinan, collagen, gelatin, zein, gluten, soy protein isolate, whey protein isolate, casein, and mixtures thereof.

Also, saliva stimulating agents, plasticizing agents, cooling agents, surfactants, emulsifying agents, thickening agents, binding agents sweeteners, flavoring, coloring agents, preservatives, or taste masking resins may be employed in the oral films or thin strips. Preferred agents include: pullulan, triethanol amine stearate, methyl cellulose, starch, triacetin, polysorbate 80, xanthan gum, maltitol, sorbitol and glycerol.

The presently described technology also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of the present technology can include other suitable agents such as flavoring agents, preservatives and antioxidants. Such antioxidants would be food acceptable and could include, for example, vitamin E, carotene, BHT or other antioxidants known to those of skill in the art.

Other compounds which may be included are, for example, medically inert ingredients, e.g., solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient. Suitable oral dosages of the prodrugs of the presently described technology can be the equivalents of those typically found in amphetamine treatments. Typical dosages for amphetamine salts can range from about 1 mg to about 100 mg, although higher dosages may be approved at later dates. Using the molecular weight of the prodrug of the present technology, the release percentage (% release) of amphetamine from the prodrug and desired dosage forms of the required amphetamine, the following equation can be generated:

grams of a prodrug needed=(dosage/molecular weight of amphetamine)(% release)(molecular weight of the prodrug)

Tablets, capsules, oral films, and other forms of presentation provided in discrete units conveniently contain a daily dose, or an appropriate fraction thereof, of one or more of the compounds of the invention. For example, units may contain from about 1 mg to about 500 mg, alternatively from about 5 mg to about 250 mg, alternatively from about 10 mg to about 100 mg of one or more of the compounds of the presently described technology.

It is also possible for the dosage form of the present technology to combine any forms of release known to persons of ordinary skill in the art. These conventional release forms include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the present technology may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the present technology may be provided in a blister pack or other such pharmaceutical package. Further, the compositions of the present technology may further include or be accompanied by indicia allowing individuals to identify the compositions as products for a prescribed treatment. The indicia may additionally include an indication of the above specified time periods for administering the compositions. For example, the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the present technology can be demonstrated using standard pharmacological models that are known in the art. Furthermore, it will be appreciated that the compositions of the present technology can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

In one or more embodiments of the present technology, the solubility and dissolution rate of the composition can be substantially changed under different physiological conditions encountered, for example, in the intestine, at mucosal surfaces, or in the bloodstream. In one or more embodiments of the present technology, the solubility and dissolution rate of the composition can substantially decrease the bioavailability of the amphetamine, particularly at doses above those intended for therapy. In one embodiment of the present technology, the decrease in bioavailability occurs upon intranasal administration. In another embodiment, the decrease in bioavailability occurs upon intravenous administration.

For each of the described embodiments of the present technology, one or more of the following characteristics can be realized: The cardiovascular toxicity of the amphetamine prodrug is substantially lower than that of the unconjugated amphetamine and amphetamine conjugated with a standard amino acid. The covalently bound non-standard amino acid moiety reduces or eliminates the possibility of behavioral deterioration or the rebound effect. The covalently bound non-standard amino acid moiety reduces or eliminates the possibility of abuse by intranasal administration. The covalently bound non-standard amino acid moiety reduces the possibility of abuse by injection.

The presently described technology further provides methods for altering and/or delivering amphetamines in a manner that can decrease their potential for abuse. Methods of the present technology provide various ways to regulate pharmaceutical dosage through conjugating amphetamine with non-standard amino acids.

One embodiment provides a method for preventing behavioral deterioration or the rebound effect by administering to a patient in need an amphetamine prodrug composition of the present technology, which comprises at least one non-standard amino acid conjugate of amphetamine.

Another embodiment provides a method for safely delivering amphetamine comprising providing a therapeutically effective amount of at least one non-standard amino acid conjugate of amphetamine wherein the non-standard amino acid moiety can reduce the rate of absorption of amphetamine as compared to delivering the unconjugated amphetamine or amphetamine conjugated with a standard amino acid.

Another embodiment provides a method for reducing amphetamine cardiovascular toxicity comprising providing a patient with at least one non-standard amino acid conjugate of amphetamine, wherein the amino acid moiety can decrease the rate of release of amphetamine within the first a few hours of administration.

Another embodiment provides a method for reducing amphetamine cardiovascular toxicity comprising providing a patient with at least one non-standard amino acid conjugate of amphetamine, wherein the amino acid moiety can provide a serum release curve which does not increase above the amphetamine's cardiovascular toxicity level.

Another embodiment provides a method for reducing bioavailability of amphetamine or for preventing a toxic release profile of amphetamine in a patient, comprising providing at least one non-standard amino acid conjugate of amphetamine, wherein the conjugated amphetamine can maintain a steady-state serum release curve which provides a therapeutically effective bioavailability but prevents spiking or increased blood serum concentrations compared to amphetamine conjugated with a standard amino acid.

Another embodiment provides a method for preventing a $C_{max}$, or equivalent $C_{max}$ spike for amphetamine while still providing a therapeutically effective bioavailability curve comprising the step of administering to a patient at least one non-standard amino acid conjugate of amphetamine.

Another embodiment of the present technology is a method for reducing or preventing abuse of amphetamine comprising providing, administering, consuming, or prescribing a composition to a patient in need thereof, wherein said composition comprises at least one non-standard amino acid conjugate of amphetamine such that the pharmacological activity of amphetamine is decreased when the composition is used in a manner inconsistent with the manufacturer's instructions.

Another embodiment of the present technology is a method of preventing behavioral deterioration or the rebound effect of amphetamine or stimulant treatment comprising providing, administering, consuming, or prescribing an amphetamine composition of the presently described technology to a patient in need thereof, wherein said composition comprises at least one non-standard amino acid conjugate of amphetamine that can decrease the potential of behavioral deterioration or the rebound effect from amphetamine or stimulant treatment.

Another embodiment of the present technology is a method for reducing or preventing the euphoric effect of amphetamine comprising providing, administering, or prescribing to a human in need thereof, or consuming a composition comprising at least one non-standard amino acid conjugate of amphetamine that can decrease the pharmacological activity of amphetamine when the composition is used in a manner inconsistent with the manufacturer's instructions.

Another embodiment of the present technology is any of the preceding methods wherein the amphetamine composition used is adapted for oral administration, and wherein the amphetamine prodrug is resistant to release amphetamine from the non-standard amino acid moiety when the composition is administered parenterally, such as intranasally or intravenously. Preferably, amphetamine may be released from the non-standard amino acid moiety in the presence of the intestinal tract. Optionally, the amphetamine composition used may be in the form of a tablet, capsule, oral film, oral solution, oral suspension, or other oral dosage form discussed herein.

For one or more of the recited methods, the composition of the present technology used may yield a therapeutic effect without substantial euphoria. Preferably, the amphetamine composition of the present technology can provide a therapeutically bioequivalent AUC when compared to other controlled release amphetamine compositions but does not provide a $C_{max}$, which results in euphoria or an equivalent $C_{max}$.

For one or more of the recited methods of the present technology, the following properties may be achieved through conjugating amphetamine to a non-standard amino acid. In one embodiment, the cardiovascular toxicity or stress of the non-standard amino acid conjugate of amphetamine of the present technology may be lower than that of the amphetamine when the amphetamine is delivered in its unconjugated state, as a compound conjugated to a standard amino acid, or as a salt thereof. In another embodiment, the possibility of behavioral deterioration is reduced or eliminated. In another embodiment, the possibility of abuse by intranasal administration is reduced or eliminated. In another embodiment, the possibility of abuse by intravenous administration is reduced or eliminated.

Another embodiment of the present technology provides methods of treating various diseases or conditions requiring the stimulation of the central nervous system (CNS) comprising administering compounds or compositions of the present technology which, optionally, further comprise commonly prescribed active agents for the respective illness or disease. For instance, one embodiment of the invention comprises a method of treating attention deficit hyperactivity disorder (ADHD) comprising administering to a patient at least one non-standard amino acid conjugate of amphetamine. Another embodiment provides a method of treating attention deficit disorder (ADD) comprising administering to a patient compounds or compositions of the invention.

Another embodiment of the invention provides a method of treating narcolepsy comprising administering to a patient compounds or compositions of the presently described technology.

The presently described technology and its advantages will be better understood by reference to the following examples. These examples are provided to describe specific embodiments of the present technology. By providing these specific examples, the applicants do not limit the scope and spirit of the present technology. It will be understood by those skilled in the art that the full scope of the presently described technology encompasses the subject matter defined by the claims appending this specification, and any alterations, modifications, or equivalents of those claims.

Example 1

Comparative Study of Pharmacokinetic Parameters of Released d-Amphetamine Following Administration of a Non-Standard Amino Acid Conjugate (hArg-Amp) and a Standard Amino Acid Conjugate (Vyvanse™, Lys-Amp)

The pharmacokinetic parameters of d-amphetamine following oral administration of a non-standard amino acid conjugate of the present technology and a standard amino acid conjugate, Vyvanse™ (Lys-Amp), commercially available from Shire, Incorporated of Wayne, Pa. are studied in this example. The non-standard amino acid conjugate used in this example is the hydrochloride salt of hArg-Amp. The results are recorded in the table below:

TABLE 1

| Parameter | Non-standard amino acid % amp[1] | Vyvanse ™ % total Amp[2] |
|---|---|---|
| $AUC_{0-8\,h}$ | 94% | 100% |
| $AUC_{0-4\,h}$ | 77% | 100% |
| $AUC_{inf}$ | 95% | 100% |
| $C_{max}$ | 76% | 100% |
| $T_{max}$ | 400% | 100% |

[1]Percent amphetamine released relative to Vyvanse ™ (at an equimolar concentration of amphetamine contained in the non-standard amino acid prodrug compared to the total amphetamine contained in Vyvanse ™)
[2]Percent amphetamine relative to 50 mg Vyvanse ™ dose The study shows that the $C_{max}$ of a prodrug of the preset technology is significantly lower than that of Vyvanse™, a standard amino acid conjugate of d-amphetamine, which can lead to lower cardiovascular effects (blood pressure, heart rate). Quick release (higher $C_{max}$) of amphetamine has already demonstrated significant increases in blood pressure and heart rate. In certain patient populations, these cardiovascular side effects can be dose limiting or can cause the termination of stimulant therapy.

The pharmacokinetic parameters of d-amphetamine following parental administration of hArg-Amp and d-amphetamine are also studied. The study shows that little release of amphetamine (<50%) happens when hArg-Amp is taken through parental routes (intranasal, intravenous) due to differences in enzymes encountered in gut versus other routes. When Adderall X® or other controlled release formulations of amphetamine are injected or snorted, the pharmacokinetic parameters of the amphetamine are significantly altered and an individual can use these changes to produce euphoria.

Example 2

Preparation of Boc-Orn(Boc)-Amp

Boc-Orn(Boc)-OH (1.5 g, 4.518 mmol) was dissolved in DMF (15 ml). EDCI (1.299 g, 6.777 mmol), NHS (0.572 g, 4.969 mmol), d-amphetamine (0.732 g, 5.422 mmol) and DIEA (0.87 ml, 4.969 mmol) were then added sequentially. The clear reaction mixture was stirred at room temperature for 16 hours (hrs). The reaction mixture was quenched with pH 3 water (40 ml), and the product was extracted with EtOAc (3×70 ml). The combined extracts were washed with pH 3 water, saturated NaHCO$_3$ followed by water. The EtOAc layer was dried over anhydrous Na$_2$SO$_4$. Solvent was removed to obtain 1.82 g of protected amide as a white solid.

The white solid was analyzed by $^1$H NMR (CDCl$_3$) δ. The results show 1.1-1.2 (m, 3H, Amp α-CH$_3$), 1.3-1.5 (m, 18H, Boc CH$_3$), 1.6-1.8 (m, 4H, Orn β, γ CH$_2$), 2.75 (m, 2H, Amp β CH$_2$), 3.05-3.1 (m, 2H, Orn δ CH$_2$), 3.2 (m, 1H, Amp α CH), 4.1 (m, 1H, Orn α CH), 7.1-7.4 (m, 5H, Amp Ar—H). These NMR shifts are consistant with the structure of Orn-Amp.

Example 3

Preparation of Orn-Amp

Boc-Orn(Boc)-Amp (1.35 g, 3 mmol) was dissolved in EtOAc (200 ml) and to the slightly cloudy solution was added MsOH (0.43 ml, 6.6 mmol) drop wise. The reaction mixture became a clear solution which was stirred at room temperature for approximately 20 hrs. Solvent was removed and the residue was triturated in hexanes. Off-white solid product was formed which was filtered under vacuum and washed with hexanes. The solid was dried in vacuum oven for 20 hrs to obtain 0.88 g of Orn-Amp-2MsOH (l-ornithine-d-amphetamine dimesylate).

The product obtained was tested by $^1$H NMR (DMSO-d$_6$) δ. The result shows 1.1 (m, 3H, Amp α-CH$_3$), 1.4-1.6 (m, 4H, Orn β, γ CH$_2$), 2.35 (s, 6H, CH$_3$SO$_3$H CH$_3$), 2.6-2.8 (m, 4H, Amp β and Orn δ), 3.75 (m, 1H, Amp α), 4.05 (m, 1H, Orn α), 7.1-7.3 (m, 5H, Amp Ar—H), 7.6-8.5 (br peaks, amide and amine); $^{13}$C NMR (DMSO-d$_6$) δ 18.45 (Orn γ), 21.49 (Orn β), 27.30 (Amp β), 37.38 (Amp CH$_3$), 37.77 (Amp α), 41.20 (Orn δ), 51.54 (Orn α), 125.29 (p-Ar), 127.27 (m-Ar), 129.17 (o-Ar), 137 (Ar), 166.58 (C=O); M+1=250.7. These results are consistent with the proposed structure.

Example 4

Preparation of Boc-hArg(NO$_2$)-Amp

Boc-hArg(NO$_2$)—OH (2.667 g, 8 mmol) was dissolved in DMF (25 ml). EDCI (2.30 g, 12 mmol), NHS (1.012 g, 8.8 mmol), d-amphetamine (1.269 g, 9.6 mmol) and DIEA (1.138 g, 8.8 mmol) were then added sequentially. The clear reaction mixture was stirred at room temperature for 16 hrs. The reaction mixture was quenched with pH 3 water (150 ml), and the product was extracted with EtOAc (3×50 ml). The combined extracts were washed with pH 3 water followed by saturated NaCl. The EtOAc layer was dried over anhydrous MgSO$_4$. The product was recrystallized from EtOAc-Hexane two times to give 2.36 g of desired protected product.

The product was analyzed using $^1$H NMR (DMSO-d$_6$) δ. The result shows 0.9-1.1 (m, 3H, Amp CH$_3$), 1.1-1.2 (m, 2H, hArg γ CH$_2$), 1.2-1.5 (m, 13H, Boc CH$_3$, hArg β,δ CH$_2$), 2.55-2.75 (m, 2H, Amp β CH$_2$), 3.1 (m, 2H, hArg ε CH$_2$), 3.75 (m, 1H, Amp α CH), 3.95 (m, 1H, hArg α CH), 6.65 (t, 1H, hArg guanidino NH), 7.1-7.3 (m, 5H, Amp Ar—H), 7.6-8.2 (br m, 2H, hArg guanidine NH and amide NH), 8.5 (br s, 1H, hArg NH—NO$_2$). These results would be considered consistent with the proposed structure.

Example 5

Preparation of hArg-Amp-2HCl
(l-homoarginine-d-amphetamine Dihydrochloride)

Boc-hArg(NO$_2$)-Amp (1.5 g) was dissolved in HPLC grade MeOH (120 ml) and to the clear solution was added the Pd—C catalyst (10%, Aldrich). A small stir bar was placed in the flask and the reaction mixture was stirred under a slow stream of hydrogen overnight after incorporating the 5-6N HCl in 2-propanol solution (1.5 ml). After the overnight reaction, the solution was filtered and the solvent evaporated. The white crystalline product was dried under vacuum to give 1.61 g of the Boc-hArg-Amp intermediate product.

The product (1.6 g) was dissolved in 80 ml of HPLC grade MeOH, and 5-6N HCl in 2-propanol (3.2 mL) was added to the solution. The reaction mixture was stirred overnight, solvent removed and re-dissolved in minimum amount of MeOH. The final product was crashed out with MTBE, and dried under vacuum at 30° C. for about 20 hours to yield 1.12 g of a white powder.

The white powder was analyzed using $^1$H NMR (DMSO-d$_6$) δ. The result shows 0.9-1.1 (m, 3H, Amp CH$_3$), 1.1-1.2 (m, 2H, hArg γ CH$_2$), 1.35 (m, 2H, hArg β CH$_2$), 1.55 (m, 2H, hArg δ CH$_2$), 2.75 (d, 2H, Amp β CH$_2$), 3.0 (m, 2H, hArg ε CH$_2$), 3.75 (m, 1H, Amp α CH), 4.05 (m, 1H, hArg α CH), 7.1-7.2 (m, 5H, Amp Ar—H), 7.2-7.8 (br m, 3H, amide NH, HCl), 8.0 (t, 1H, hArg guanidino NH), 8.2 (br s, 2H, amide or guanidino NH$_2$), 8.75 (d, 1H, amide NH); $^{13}$C NMR (DMSO-d$_6$) δ 21.08 (Amp CH$_3$), 21.36 (hArg γ), 28.23 (hArg δ), 32.28 (hArg β), 40.18 (Amp β), 42.19 (hArg ε), 46.88 (Amp α), 52.23 (hArg α), 126.54 (β-Ar), 128.52 (m-Ar), 129.60 (o-Ar), 139.34 (Ar), 157.61 (C=O), 167.95 (guanidino C); M+1=306. These results would be considered to be consistant with the proposed structure.

Example 6

Preparation of Cit-Amp•HCl
(l-citrulline-d-amphetamine hydrochloride)

Boc-Cit-OH (0.50$_0$ g, 1.82 mmol) was dissolved in anhydrous THF. To this solution was added NHS (0.209 g, 1.82 mmol) followed by DCC (0.376 g, 1.8$_2$ mmol). Resulting slurry was stirred at ambient temperature overnight. In a separate flask, d-amphetamine sulfate (0.306 g, 0.83 mmol) was suspended in THF (10 ml) and NMM (0.34 ml, 3.64 mmol) was added. The activated ester was filtered directly into the amphetamine suspension and the resulting suspension was stirred overnight. The reaction was quenched with 5% NaHCO$_3$ and IPAC for 45 min. Organic solvent was then removed. The aqueous layer was then extracted 3 times with IPAC and the combined organics were washed with 5% acetic acid, 5% NaHCO$_3$ and 5% NaCl. The organic layer was then dried over NaSO$_4$ and solvent was removed. Crude product was re-crystallized using IPAC/heptane to yield 200 mg of a white solid.

10 ml of 4N HCl in dioxane were added to the 200 mg (0.200 g) Boc-Cit-Amp. The mixture was stirred at room temperature for 6 hours and solvent was removed.

Example 7

Comparative Biological Study of Lys-Amp and hArg-Amp

Male Sprague-Dawley rats were fasted overnight and dosed by oral gavage with either l-homoarginine-d-amphetamine (hArg-Amp) or l-lysine-d-amphetamine (Vyvanse™, Lys-Amp). Water was provided ad libitum. Doses were calculated at an equivalent 1.5 mg/kg freebase equivalent of d-amphetamine. Plasma concentrations of d-amphetamine were measured using ELISA (Neogen Corp. Lexington, Ky.).

Mean plasma concentration curves (n=5) of d-amphetamine released by l-homoarginine-d-amphetamine or l-lysine-d-amphetamine are shown in FIG. 1. Pharmacokinetic (PK) parameters of this study are listed in Table 2.

TABLE 2

Pharmacokinetic Properties of hArg-Amp and Lys-Amp

| Vehicle | % AUC | Tmax | Cmax | % Tmax | % Cmax |
|---|---|---|---|---|---|
| Lys-Amp | 100% | 3 h | 44 ng/ml | 100% | 100% |
| hArg-Amp | 99% | 4 h | 44 ng/ml | 133% | 100% |

This pharmacokinetic (PK) study clearly demonstrates a shift in the $T_{max}$ for the non-standard amino acid (hArg-Amp) compared to the standard amino acid (Lys-Amp). This shift may be due to a reduction in the rate of enzymatic hydrolysis of the amide bond of the non-standard amino acid attached to amphetamine vs. the standard amino acid attached to amphetamine.

Figure 2:
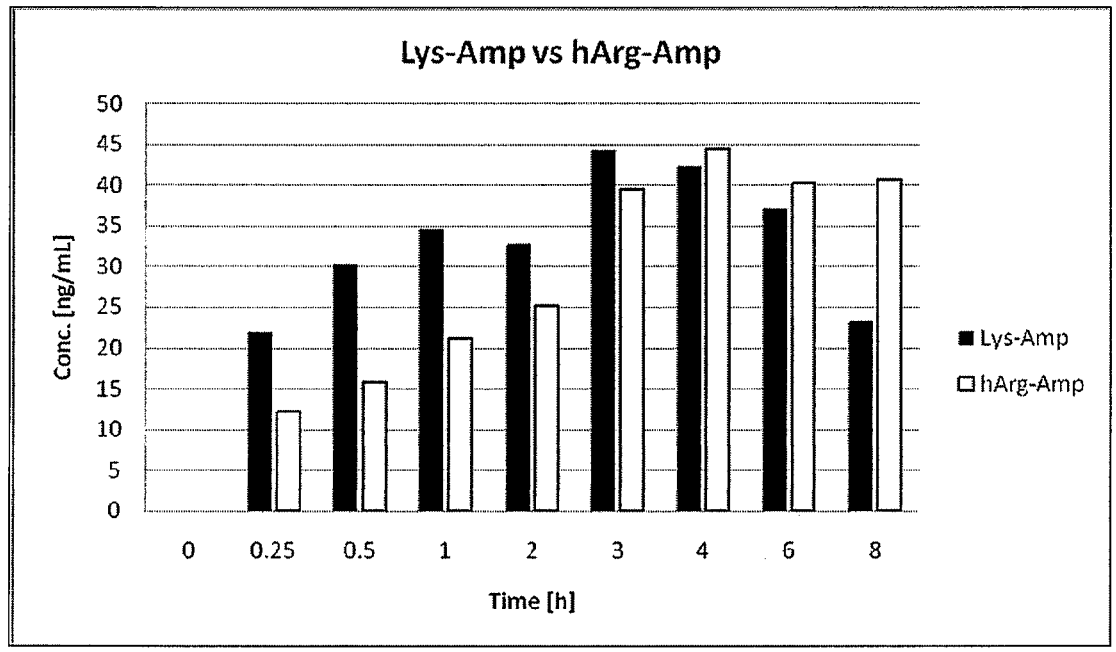
FIG. 2 shows the relative blood levels of d-amphetamine released from both Lys-Amp and hArg-Amp in the study described in FIG. 1 and Table 2.
Figure 3:
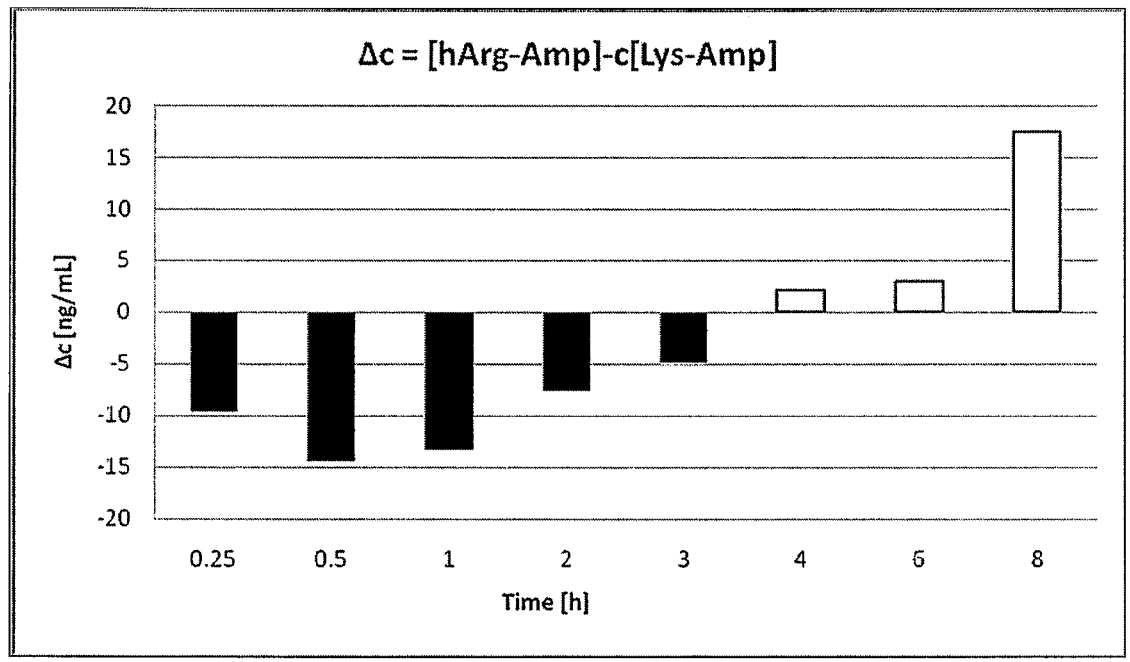
FIGS. 3 and 4 show the difference in blood levels obtained from the study described in FIG. 2.
Figure 4:
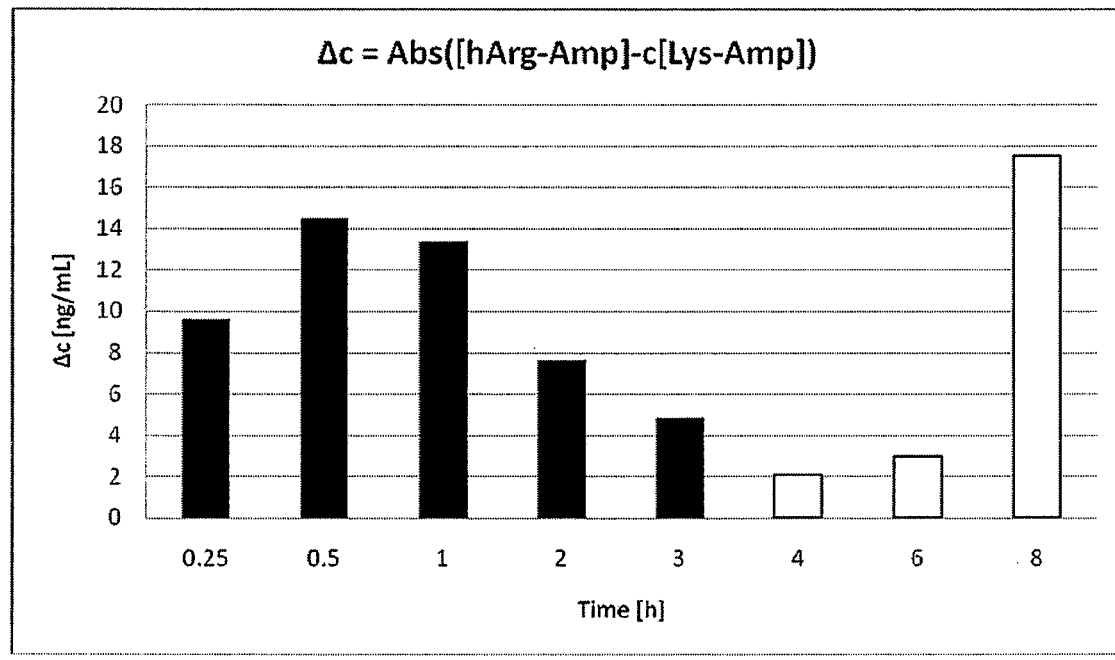

FIGS. 2-4 represent different ways to view the data reflected in FIG. 1 and Table 2. As further discussed below, these figures highlight the differences of hArg-Amp over Lys-Amp during the first several hours.

FIG. 2 demonstrates the relative blood levels of d-amphetamine released from both Lys-Amp and hArg-Amp. The graph shows that equivalent blood levels do not occur until later time points and that blood levels do not appear to spike or have a more significant $C_{max}$ than Lys-Amp. The amount of d-amphetamine released from hArg-Amp is gradual and maintains a more steady concentration over the duration of the study than did Lys-Amp. In contrast, Lys-Amp blood levels of released d-amphetamine "spiked" at 3 hours and cleared more quickly than the blood levels obtained from hArg-Amp.

FIGS. 3 and 4 show the difference in blood levels obtained from the study described in FIG. 2. As is shown, the initial blood levels for both conjugates (Lys-Amp and hArg-Amp) are very different, with hArg-Amp releasing amphetamine at a more gradual rate. These differences in blood levels become less during the more critical duration of action for stimulant treatments and more importantly, the differences are greater again at later time points suggesting that hArg-Amp maintains a more consistent dose of amphetamine when compared to Lys-Amp. The longer duration of release for hArg-Amp would suggest a much lower opportunity for behavioral deterioration to occur.

Figure 5:
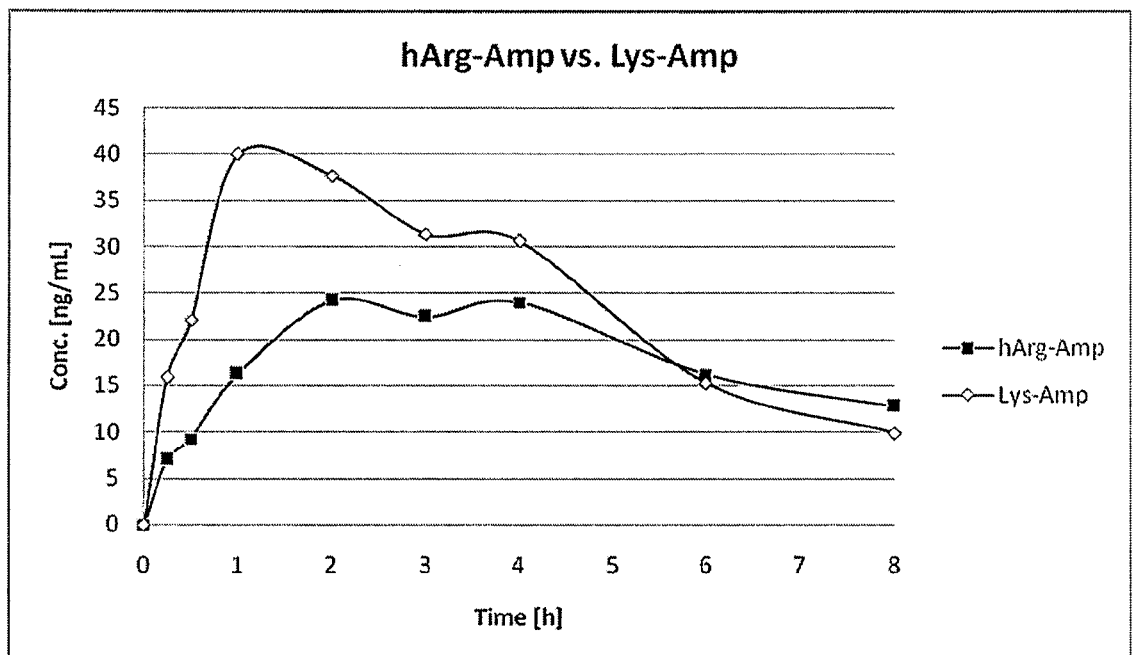
FIG. 5 shows the average pharmacokinetic (PK) results of the other oral studies in Example 7 for four (4) oral studies (n=20 per vehicle) of l-homoarginine-d-amphetamine and l-lysine-d-amphetamine.

Other oral studies have been conducted in a similar fashion and are summarized in Table 3 below. The average PK results for four (4) oral studies (n=20 per vehicle) are recorded in FIG. 5:

TABLE 3

Average Results of 4 Oral Studies (n = 20 per compound)

| Vehicle | % AUC | Tmax | % Tmax | % Cmax | % AUC 0-4 h |
|---|---|---|---|---|---|
| Lys-Amp | 100% | 1 h | 100% | 100% | 100% |
| hArg-Amp | 94% | 4 h | 400% | 76% | 77% |

Example 8

Biological Study of hArg-Amp and Orn-Amp

Figure 6:
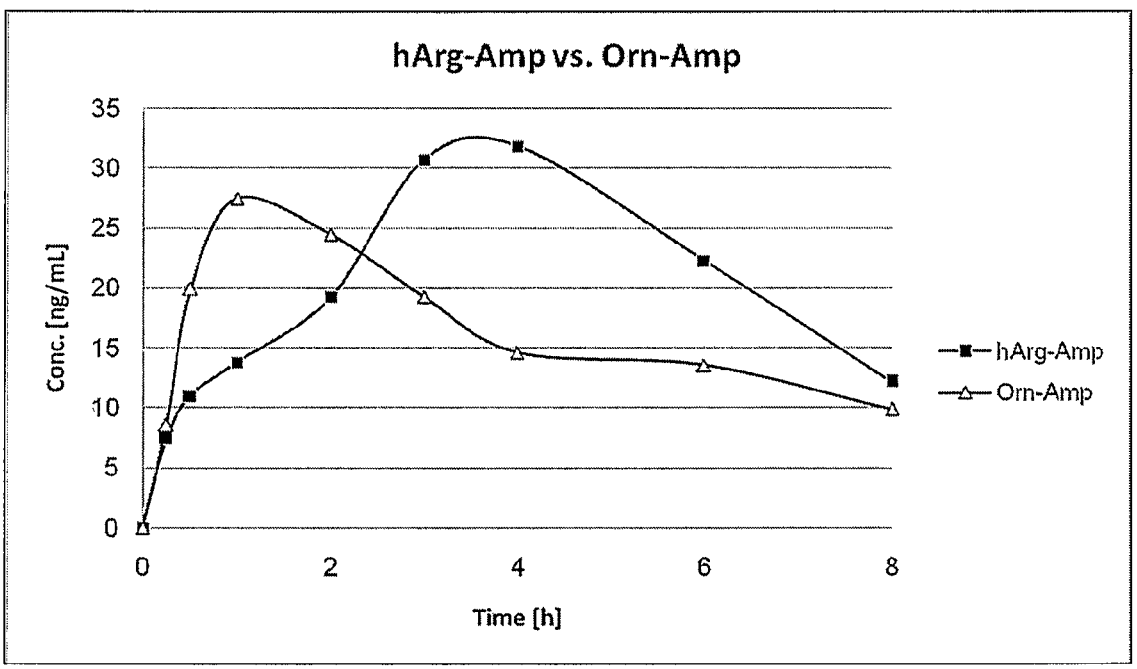
FIG. 6 shows the mean plasma concentration curves (n=5) of d-amphetamine released by hArg-Amp or Orn-Amp in the oral pharmacokinetic study of Example 8.

To compare the amount of release of d-amphetamine among various non-standard amino acids, l-ornithine-d-amphetamine (Orn-Amp) was dosed in replace of Lys-Amp in Example 7 in another oral pharmacokinetic study. Mean plasma concentration curves (n=5) of d-amphetamine released by hArg-Amp or Orn-Amp are shown in FIG. 6. Pharmacokinetic parameters of this study are listed in Table 4.

TABLE 4

Pharmacokinetic Properties of hArg-Amp and Orn-Amp

| Vehicle | % AUC | Tmax | Cmax | % Tmax | % Cmax |
|---|---|---|---|---|---|
| hArg-Amp | 100% | 4 h | 32 ng/ml | 100% | 100% |
| Orn-Amp | 78% | 1 h | 27 ng/ml | 25% | 84% |

Example 9

Comparative Biological Study of Lys-Amp hArg-Amp, Orn-Amp and Cit-Amp

Figure 7:
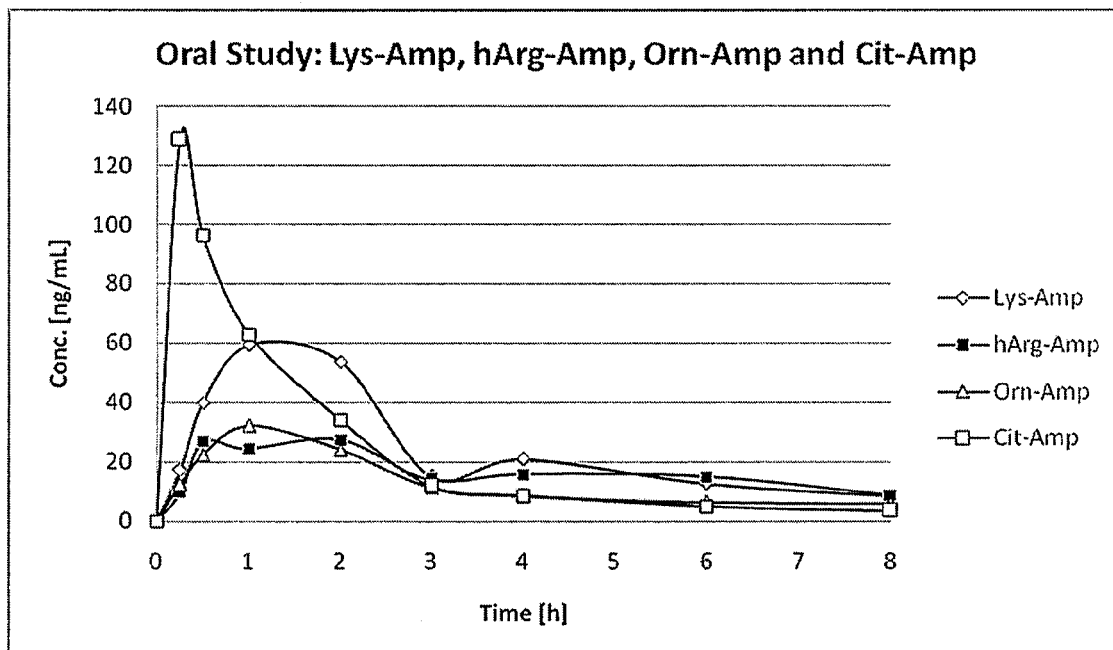
FIG. 7 shows the mean plasma concentration curves (n=5) of d-amphetamine released by hArg-Amp, Orn-Amp and Cit-Amp in the oral pharmacokinetic study of Example 9.

To compare the amount of release of d-amphetamine among various non-standard amino acids, l-ornithine-d-amphetamine (Orn-Amp), hArg-Amp and l-citrulline-d-amphetamine (Cit-Amp) were dosed with Lys-Amp in another oral pharmacokinetic study. Mean plasma concentration curves (n=5) of d-amphetamine released by hArg-Amp, Orn-Amp and Cit-Amp are shown in FIG. 7. Pharmacokinetic parameters of this study are listed in Table 5.

Direct comparison of 3 non-standard amino acid conjugates of amphetamine (Cit, Orn and hArg) demonstrate the significant ability to shift or change the pharmacokinetic properties versus the standard amino acids. All non-standard amino acids studied released amphetamine in an amount greater than 50%. Ornithine and homoarginine both showed $C_{max}$ levels far below that of lysine and both homoarginine and citrulline significantly shifted the $T_{max}$ compared to Lys-Amp. These changes to the pharmacokinetic properties of amphetamine when conjugated to non-standard amino acids represent clinically significant changes not described or demonstrated by Lys-Amp nor described or demonstrated by other standard amino acids.

TABLE 5

Oral Properties of Lys-Amp, hArg-Amp, Orn-Amp and Cit-Amp

| Vehicle | % AUC | Tmax | Cmax | % Tmax | % Cmax |
|---|---|---|---|---|---|
| Lys-Amp | 100% | 1 h | 59 ng/ml | 100% | 100% |
| hArg-Amp | 68% | 2 h | 27 ng/ml | 200% | 46% |
| Orn-Amp | 52% | 1 h | 32 ng/ml | 100% | 54% |
| Cit-Amp | 95% | 15 m | 129 ng/ml | 25% | 219% |

Example 10

Intranasal Study of Amp, hArg-Amp, Orn-Amp

Figure 8:
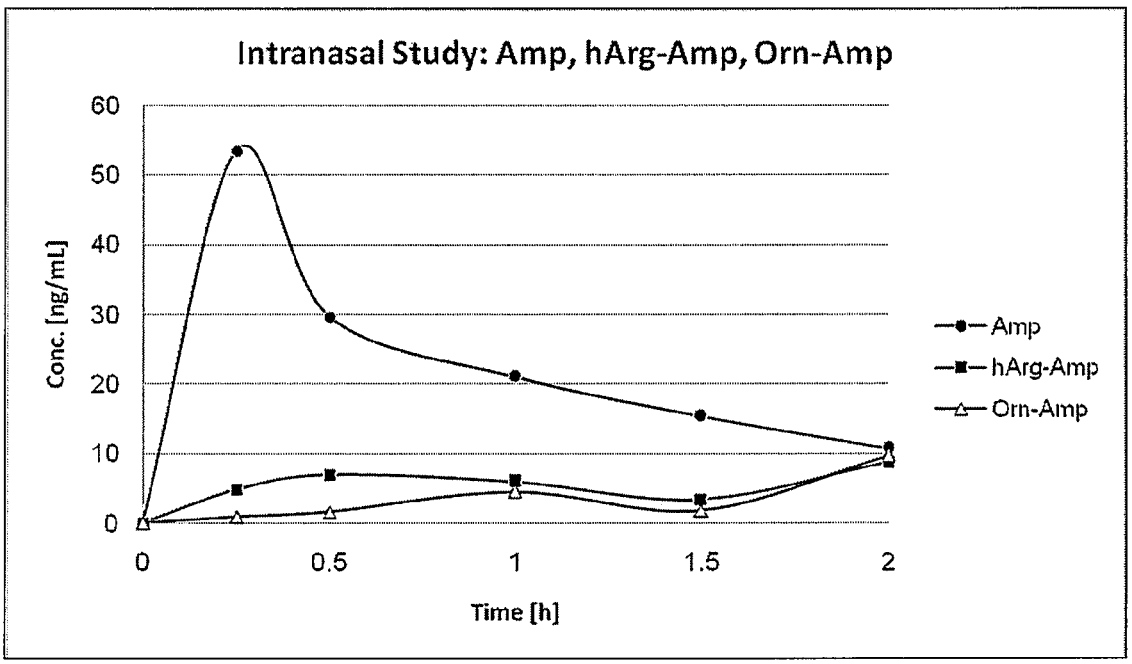
FIG. 8 shows the mean plasma concentration curves (n=5) of d-amphetamine released by hArg-Amp or Orn-Amp in the intranasal study of Example 10.

Male Sprague-Dawley rats were fasted overnight and dosed by intranasal administration with either hArg-Amp, Orn-Amp or d-amphetamine. Doses were calculated at an equivalent 1.5 mg/kg freebase equivalent of d-amphetamine. Plasma concentrations of d-amphetamine were measured using ELISA. Mean plasma concentration curves (n=5) of d-amphetamine released by hArg-Amp or Orn-Amp are shown in FIG. 8. Pharmacokinetic parameters of this study are listed in Table 6. No significant release (<25%) was observed in either hArg-Amp or Orn-Amp.

TABLE 6

Intranasal Properties of d-Amp, hArg-Amp and Orn-Amp

| Vehicle | % AUC | Tmax | Cmax | % Tmax | % Cmax |
|---|---|---|---|---|---|
| d-amp | 100% | 15 m | 53 ng/ml | 100% | 100% |
| hArg-Amp | 23% | 2 h | 9 ng/ml | 1600% | 17% |
| Orn-Amp | 14% | 2 h | 10 ng/ml | 1600% | 19% |

Example 11

Intravenous Study of Amp, hArg-Amp, Orn-Amp

Figure 9:
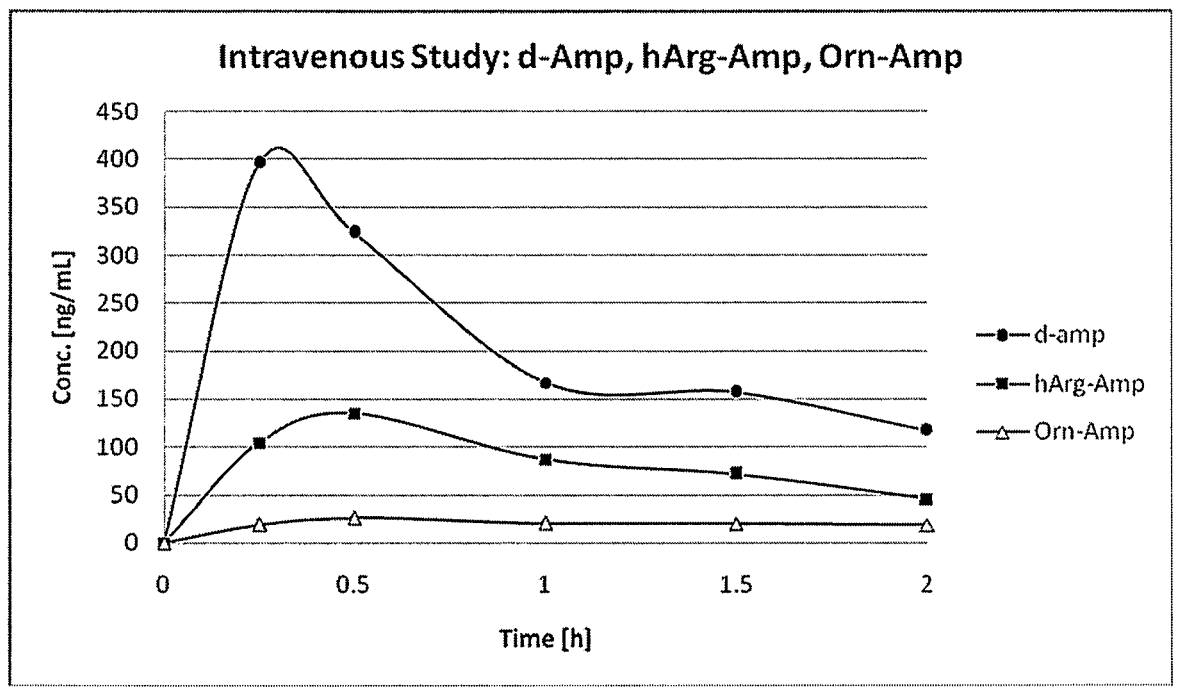
FIG. 9 shows the mean plasma concentration curves (n=5) of d-amphetamine released by hArg-Amp or Orn-Amp in the intranasal study of Example 11.

Male Sprague-Dawley rats were dosed by intravenous administration through the tail vein with hArg-Amp, Orn-Amp or d-amphetamine. Doses were calculated at an equivalent 1.5 mg/kg freebase equivalent of d-amphetamine. Plasma concentrations of d-amphetamine were measured using ELISA. Mean plasma concentration curves (n=5) of d-amphetamine released by hArg-Amp or Orn-Amp are shown in FIG. 9. Pharmacokinetic parameters of this study are listed in Table 7. No significant release (<35%) was observed in either hArg-Amp or Orn-Amp. The initial spike in d-amphetamine released from hArg-Amp cleared quickly while as in the intranasal study, Orn-Amp had a slight increase at the 2 hour point.

TABLE 7

Intravenous Properties of d-Amp, hArg-Amp and Orn-Amp

| Vehicle | % AUC | Tmax | Cmax | % Tmax | % Cmax |
|---|---|---|---|---|---|
| d-amp | 100% | 15 m | 396 ng/ml | 100% | 100% |
| hArg-Amp | 41% | 15 m | 135 ng/ml | 100% | 34% |
| Orn-Amp | 10% | 15 m | 26 ng/ml | 100% | 7% |

Results of the studies in Examples 7-11 clearly show an unexpected change in the oral pharmacokinetic properties by using non-standard amino acids over standard amino acids. By changing the non-standard amino acid attached to amphetamine, the conjugates are able to shift $T_{max}$ (earlier or later), modify curve shape, lower $C_{max}$, and raise $C_{max}$. In addition, the shift in $T_{max}$ for hArg-Amp may be clinically significant in that many of the cardiovascular side effects and toxicity are related to $T_{max}$ and $C_{max}$. The results demonstrate that by using non-standard amino acids a shift in the $T_{max}$, with a lower $C_{max}$ occurs without changing AUC significantly. In addition, the slope of uptake of hArg-Amp vs. Lys-Amp appears to be more gradual thus leading to a slower onset which could further alleviate side effects.

The amphetamine conjugate, hArg-Amp, of the present technology demonstrates that by using non-standard amino acids, a shift in the $T_{max}$ occurs while still retaining AUC and potential clinical effect. By using non-standard amino acids, we are able to demonstrate that both hArg-Amp and Orn-Amp show little release via the IN and IV route yet still maintain a similar AUC.

The presently described technology is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the invention as set forth in the appended claims.

What is claimed is:

1. A composition for treating a human or animal patient having attention deficit hyperactivity disorder, comprising at least one conjugate, the conjugate comprising amphetamine and homoarginine; a salt of the conjugate thereof, or a combination thereof.

2. The composition of claim 1, wherein the composition has a reduced pharmacological activity when administered by parenteral routes.

3. The composition of claim 1, wherein the salt of the conjugate is a mesylate, a hydrochloride salt, a sulfate, an oxalate, a triflate, a citrate, a malate, a tartarate, a phosphate, a nitrate, a benzoate, or a mixture thereof.

4. The composition of claim 1, wherein the composition is in the form of a tablet, a capsule, a caplet, a troche, a lozenge, an oral powder, a solution, a oral film, a thin strip, or a suspension.

5. The composition of claim 4, wherein the tablet, troche, or lozenge is chewable.

6. The composition of claim 1, wherein the conjugate, the salt of the conjugate, or the combination thereof is present in the amount of from about 1 mg to about 500 mg.

7. The composition of claim 1, wherein the conjugate, the salt of the conjugate, or the combination thereof is present in the amount of from about 5 mg to about 250 mg.

8. The composition of claim 1, wherein the conjugate, the salt of the conjugate, or the combination thereof is present in the amount of from about 10 mg to about 100 mg.

9. The composition of claim 1, wherein the conjugate, the salt of the conjugate, or the combination thereof is in an amount sufficient to provide a therapeutically bioequivalent AUC when compared to amphetamine alone, but does not provide a $C_{max}$ spike.

10. The composition of claim 1, wherein the conjugate, the salt of the conjugate, or the combination thereof is in an amount sufficient to provide a therapeutically bioequivalent AUC when compared to amphetamine alone, but does not provide an equivalent $C_{max}$.

* * * * *